IMIDAZOLIUM IONIC LIQUIDS MADE USING CARDANOL EXTRACTED FROM CASHEW NUTSHELL OIL TO ENHANCE CRUDE OIL RECOVERY IN OILFIELDS

United States Patent
Atta et al.

(10) Patent No.: US 12,194,434 B1
(45) Date of Patent: Jan. 14, 2025

(54) IMIDAZOLIUM IONIC LIQUIDS MADE USING CARDANOL EXTRACTED FROM CASHEW NUTSHELL OIL TO ENHANCE CRUDE OIL RECOVERY IN OILFIELDS

(71) Applicant: KING SAUD UNIVERSITY, Riyadh (SA)

(72) Inventors: Ayman M. Atta, Riyadh (SA); Hamad A. Al-Lohedan, Riyadh (SA); Abdelrahman O. Ezzat, Riyadh (SA); Ali K. Aldalbahi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 25 days.

(21) Appl. No.: 18/612,504

(22) Filed: Mar. 21, 2024

Related U.S. Application Data

(62) Division of application No. 18/212,034, filed on Jun. 20, 2023, now Pat. No. 11,969,708.

(51) Int. Cl.

| | |
|---|---|
| *H01M 4/48* | (2010.01) |
| *B01J 20/04* | (2006.01) |
| *B01J 20/06* | (2006.01) |
| *B01J 20/10* | (2006.01) |
| *B01J 20/26* | (2006.01) |
| *B01J 20/28* | (2006.01) |
| *B01J 20/30* | (2006.01) |
| *B01J 20/32* | (2006.01) |
| *C02F 1/28* | (2023.01) |
| *C02F 1/68* | (2023.01) |
| *C07D 233/60* | (2006.01) |
| *C08G 65/331* | (2006.01) |
| *C08G 65/333* | (2006.01) |
| *C08G 65/337* | (2006.01) |
| *E02B 15/04* | (2006.01) |
| *H01M 4/36* | (2006.01) |
| *C02F 101/32* | (2006.01) |
| *C02F 103/08* | (2006.01) |

(52) U.S. Cl.
CPC ........... *B01J 20/265* (2013.01); *B01J 20/043* (2013.01); *B01J 20/06* (2013.01); *B01J 20/103* (2013.01); *B01J 20/28009* (2013.01); *B01J 20/28016* (2013.01); *B01J 20/3085* (2013.01); *B01J 20/3204* (2013.01); *B01J 20/3221* (2013.01); *B01J 20/3287* (2013.01); *B01J 20/3293* (2013.01); *C02F 1/288* (2013.01); *C02F 1/681* (2013.01); *C07D 233/60* (2013.01); *C08G 65/3317* (2013.01); *C08G 65/33317* (2013.01); *C08G 65/337* (2013.01); *E02B 15/041* (2013.01); *C02F 1/281* (2013.01); *C02F 1/285* (2013.01); *C02F 2101/32* (2013.01); *C02F 2103/08* (2013.01)

(58) Field of Classification Search
CPC ........ B01J 20/043; B01J 20/06; B01J 20/103; B01J 20/28016; B01J 20/28009; B01J 20/3085; B01J 20/3221; B01J 20/3287; B01J 20/3293; C02F 1/288; C02F 1/681; C07D 233/60; C08G 65/33317; C08G 65/337; E02B 15/041
See application file for complete search history.

(56) References Cited

U.S. PATENT DOCUMENTS

| | | |
|---|---|---|
| 7,845,409 B2 | 12/2010 | Shinbach et al. |
| 2007/0181302 A1 | 8/2007 | Bicerano |
| 2016/0075940 A1 | 3/2016 | Rappolt |
| 2017/0349814 A1 | 12/2017 | Gupta |

FOREIGN PATENT DOCUMENTS

| | | |
|---|---|---|
| CN | 110484227 A | 11/2019 |
| CN | 112143578 A * | 12/2020 |

OTHER PUBLICATIONS

Eke et al., "Performance Evaluation of Cashew Nut Shell Liquid CNSL as Flow Improver for Waxy Crude Oils," SPE Nigeria Annual International Conference and Exhibition, Lagos, Nigeria, Aug. 2019.

* cited by examiner

*Primary Examiner* — Yong L Chu
(74) *Attorney, Agent, or Firm* — Nath, Goldberg & Meyer; Richard C. Litman

(57) ABSTRACT

Modified chemical structures of cardanol extracted from cashew nut shell oil, and the use of the same to prepare imidazolium ionic liquids (IILs). The IILs can be used to prepare different types of silica, magnetite and calcium carbonate nanoparticles (NPs) as multifunctional oilfield chemicals for use in various oil spill collection, de-emulsification, viscosity improvement, asphaltene dispersant, and enhanced oil recovery applications.

7 Claims, 13 Drawing Sheets

IMIDAZOLIUM IONIC LIQUIDS MADE USING CARDANOL EXTRACTED FROM CASHEW NUTSHELL OIL TO ENHANCE CRUDE OIL RECOVERY IN OILFIELDS

CROSS-REFERENCE TO RELATED APPLICATION

This application is a divisional of U.S. patent application Ser. No. 18/212,034, filed on Jun. 20, 2023, now U.S. Pat. No. 11,969,708, the entire disclosures of which are incorporated by reference herein.

BACKGROUND

1. Field

The disclosure of the present patent application relates to modified chemical structures of cardanol extracted from cashew nut shell oil, and the use of the same to prepare imidazolium ionic liquids.

2. Description of the Related Art

Cardanol is a naturally occurring fatty phenol extracted from Cashew nut shell liquid as an agricultural waste product that has been used as a renewable resource for oilfield chemicals. Its chemical structure has at times been modified to replace monomers and polymers produced from petrochemical feed stocks to produce biopolymers, biosurfactants, biocomposites, and nanomaterials. Recently, there has been some discussion that cardanol is a likely candidate for preparing "green" surfactant species like anionic (sulfonates), nonionic (ethoxylates and cardanol-formaldehyde ethoxylate polymers) and cationic (quaternary ammonium, pyridinium and imidazolinium derivatives) surfactants to replace petroleum based nonyl phenol surfactants. Moreover, cardanol can also be used to prepare biopolymer, polymer, ionic liquids (ILs) and nanocomposites for different petroleum applications.

Cardanol can be modified to protic ionic liquid via quaternization of its chloro etherified product with triethanol amine that can be used as a demulsifier for crude oil emulsions. Moreover, protic poly (ionic liquids) based on etherified products of cardanol with ethanol amine quaternized with 2-acrylamido-2-methylpropane sulfonic acid has also been used as a de-emulsifier for heavy crude oil emulsions. Aprotic quaternized cardanol amine salt as an ionic liquid has also been prepared. The imidazole and pyridine were linked directly on the amphiphilic cardenol derivatives to prepare imidazolium and pyridinium ILs. Cardenol derivatives have been used to prepare nanomaterials such as nanotubes, nanofibers, gels and surfactants.

Thus, new sources of cardanol and methods of using the same to produce imidazolium ionic liquids solving the aforementioned problems are desired.

SUMMARY

The present subject matter relates to new water soluble cardenol imidazolium ionic liquids as multifunctional additives to green oilfield chemicals to solve different petroleum crude oil problems that can occur during their production and transportation. In one aspect, the present subject matter relates to the preparation of metal and metal oxide nanomaterials capped with cardanol imidazolium ionic liquids to increase their efficacy as green oil-field chemicals.

In one aspect, the present subject matter is directed to the modification of the chemical structure of cardanol as a precursor to prepare a new, thermally stable imidazolium ionic liquid (IIL). The IILs can be used to prepare different types of silica, magnetite and calcium carbonate nanoparticles (NPs) as multifunctional oilfield chemicals for use in various oil spill collection, de-emulsification, viscosity improvement, asphaltene dispersant, and enhanced oil recovery applications.

In an embodiment, the present subject matter relates to a method for preparing a cardanol imidazolium ionic liquid, the method comprising: obtaining cardanol extracted from cashew nut oil; etherifying the cardanol with polyethylene glycol (PEG) to obtain a cardanoxy polyether surfactant (CEO); grafting the cardanoxy polyether surfactant (CEO) to an imidazole to obtain a grafted CEO imidazole; and quaternizing the grafted CEO imidazole to obtain a cardenyl polyethoxy imidazolium ionic liquid (CEOIm).

In one embodiment, the present subject matter relates to a cardenyl polyethoxy imidazolium ionic liquid (CEOIm) prepared according to the methods described herein.

In another embodiment, the present subject matter relates to a method for preparing a dicardenoxy imidazolium ionic liquid (DCIm), the method comprising: obtaining cardanol extracted from cashew nut oil; dissolving the cardanol in a mixture of epichlorhydrin and water to obtain CGE having the formula:

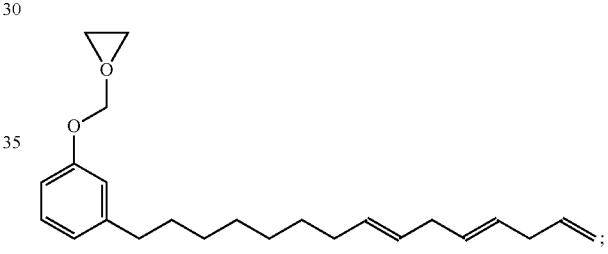

mixing the CGE with a compound of the formula $H_2N-(-CH_2-CH_2-NH)_n-H$, wherein n is an integer between 3 and 5, to obtain a cardanol amine (CIm) having the formula:

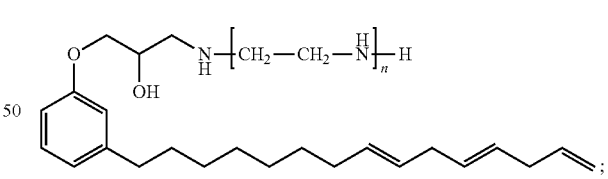

dissolving the CIm in acetic acid or trifluoroacetic acid to obtain an amine solution; and adding an aldehyde solution to the amine solution to obtain the dicardenoxy imidazolium ionic liquid (DCIm).

In one embodiment, the present subject matter relates to a dicardenoxy imidazolium ionic liquid (DCIm) prepared according to the methods described herein.

In a further embodiment, the present subject matter relates to a method for preparing a dicardnyl tri-imidazolium ionic liquid (DCTIm), the method comprising: heating the dicardenoxy imidazolium ionic liquid (DCIm) prepared herein with an alkyl halide; and obtaining the dicardnyl tri-imidazolium ionic liquid (DCTIm).

In one embodiment, the present subject matter relates to a dicardnyl tri-imidazolium ionic liquid (DCTIm) prepared according to the methods described herein.

In one more embodiment, the present subject matter relates to a method for preparing nanoparticles modified by a cardanol imidazolium ionic liquid, the method comprising: contacting nanoparticles of a substance of interest with the cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof; and obtaining the modified nanoparticles, wherein the substance of interest is selected from the group consisting of magnetite, calcium carbonate, and silica.

In yet another embodiment, the present subject matter relates to a method of preparing magnetite nanoparticles capped with a cardanol imidazolium ionic liquid, the method comprising: stirring magnetite in water; adding $NH_4OH$ to the magnetite in water to obtain a pH of about 10; adding oleic acid to obtain a ferrofluid; adding a solution of the cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in dichloromethane and ethanol with subsequent adding of an excess of ferrofluid to obtain a magnetic hybrid capped with the oleic acid as an inner layer and the cardanyl imidazolium ionic liquid as an outer layer; and separating the capped magnetic hybrid by using a magnet.

In one embodiment, the present subject matter relates to magnetite nanoparticles capped with a cardanol imidazolium ionic liquid prepared according to the methods described herein.

In still yet another embodiment, the present subject matter relates to a method of preparing modified calcium carbonate nanoparticles, the method comprising: preparing an aqueous solution of calcium carbonate ($Ca(OH)_2$) in water; adding a solution of a cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in ethanol to the aqueous solution of calcium carbonate to obtain a reaction solution; adding $CO_2$ bubbles through the reaction solution until the reaction solution reaches a pH of about 7; and separating the modified calcium carbonate nanoparticles by centrifugation, wherein the modified calcium carbonate nanoparticles are selected from the group consisting of $CaCO_3$/CEOIm, $CaCO_3$/DCIm, $CaCO_3$/DCTIm, and combinations thereof.

In one embodiment, the present subject matter relates to modified calcium carbonate nanoparticles prepared according to the methods described herein.

In one more embodiment, the present subject matter relates to a method of preparing functionalized silica nanoparticles, the method comprising: aging silica ($SiO_2$) nanoparticles with a solution of a cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in toluene, whereby the cardanyl imidazolium ionic liquid diffuses and adsorbs on a surface of the silica nanoparticles; decanting supernatant and collecting the functionalized silica nanoparticles; and separating the functionalized silica nanoparticles by centrifugation.

In one embodiment, the present subject matter relates to functionalized silica nanoparticles prepared according to the methods described herein.

In a further embodiment, the present subject matter relates to a method for dispersing oil spilled on seawater, the method comprising: applying the nanoparticles modified by a cardanol imidazolium ionic liquid prepared according to the present methods to seawater having the oil spilled thereon; and dispersing the oil spilled on the seawater.

In another embodiment, the present subject matter relates to a method for collecting spilled oil, the method comprising: applying the nanoparticles comprising magnetite nanoparticles capped with a cardanol imidazolium ionic liquid prepared according to the present methods to spilled oil; and collecting the spilled oil.

In still another embodiment, the present subject matter relates to a method for reducing viscosity of heavy crude oil, the method comprising: applying the nanoparticles modified by a cardanol imidazolium ionic liquid prepared according to the present methods to heavy crude oil, thereby reducing the viscosity of the heavy crude oil.

In one more embodiment, the present subject matter relates to a method for enhancing recovery of crude oil spilled on rock, the method comprising: applying the nanoparticles modified by a cardanol imidazolium ionic liquid prepared according to the present methods to rock having the crude oil spilled thereon; and recovering the crude oil spilled on the rock.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
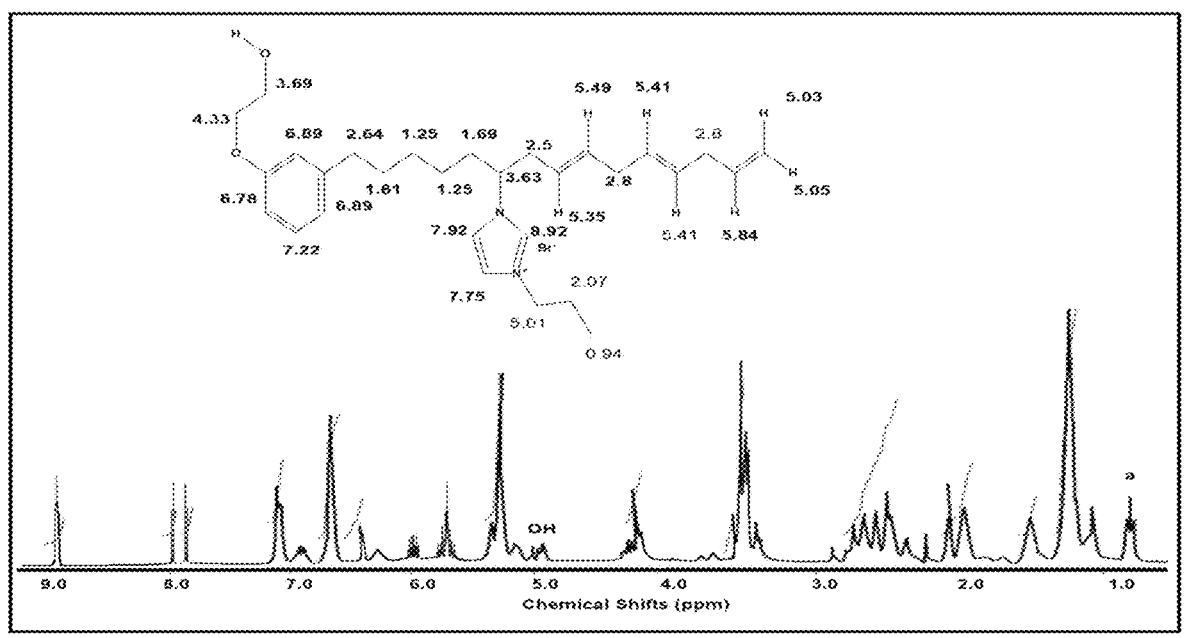
FIG. 1 is a $^1HNMR$ spectrum of CEOIm.

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to new water soluble cardenol imidazolium ionic liquids as multifunctional additives to green oilfield chemicals to solve different petroleum crude oil problems that can occur during their production and transportation. In one aspect, the present subject matter relates to the preparation of metal and metal oxide nanomaterials capped with cardanol imidazolium ionic liquids to increase their efficacy as green oil-field chemicals.

In one aspect, the present subject matter is directed to the modification of the chemical structure of cardanol as a precursor to prepare a new, thermally stable imidazolium ionic liquid (IIL). The IILs can be used to prepare different types of silica, magnetite and calcium carbonate nanoparticles (NPs) as multifunctional oilfield chemicals for use in various oil spill collection, de-emulsification, viscosity improvement, asphaltene dispersant, and enhanced oil recovery applications. The cardanyl imidazolium ionic liquids and their nanomaterials can be used to collect oil spills and modify Arabic heavy crude oil viscosity. The silica and calcium carbonate nanoparticles can enhance crude oil recovery either in dolomite or calcite rocks.

In an embodiment, the present subject matter relates to a method for preparing a cardanol imidazolium ionic liquid, the method comprising: obtaining cardanol extracted from cashew nut oil; etherifying the cardanol with polyethylene glycol (PEG) to obtain a cardanoxy polyether surfactant (CEO); grafting the cardanoxy polyether surfactant (CEO) to an imidazole to obtain a grafted CEO imidazole; and quaternizing the grafted CEO imidazole to obtain a cardenyl polyethoxy imidazolium ionic liquid (CEOIm).

In one embodiment of the present methods of obtaining a cardenyl polyethoxy imidazolium ionic liquid (CEOIm), the cardenyl polyethoxy imidazolium ionic liquid can be 1-((8E,11E)-1-(3-(2-hydroxyethoxy)phenyl)pentadeca-8,11,14-trien-6-yl)-3-propyl-1H-imidazol-3-ium bromide. This product is obtained using an alkyl bromide in the present processes.

In another embodiment of the present methods of obtaining a cardenyl polyethoxy imidazolium ionic liquid (CEOIm), in the etherifying step, the cardanol can be mixed with the polyethylene glycol in an about 1:1 molar ratio. Further in the etherifying step, the cardanol can be mixed with the PEG, β,β-dicholorodiethylether (DCDE), toluene, and NaOH pellets. In certain embodiments in this regard, about 0.1 mol of the cardanol can be mixed with about 0.1 mol of the PEG, about 0.1 mol of the DCDE, about 50 mL of the toluene, and about 0.2 mol of the NaOH pellets. Accordingly, the cardanol, PEG, DCDE and NaOH pellets can be mixed in a molar ratio of about 1:1:1:2.

In another embodiment, the etherifying step can be conducted at an elevated temperature of about 110° C. to about 130° C., about 115° C. to about 125° C., or about 120° C. with stirring under, for example, an $N_2$ atmosphere. This step can be conducted for about 5 hours, about 6 hours, about 7 hours, or more, or about 6 hours. In other embodiments, the etherifying step can further comprise removing NaCl precipitate and unreacted NaOH by filtration as well as unreacted toluene and unreacted DCDE by evaporation. The reaction product can then be mixed with an alcohol, such as by way of non-limiting example isopropanol, and a hot aqueous solution of saturated NaCl to form a salt with the unreacted PEG which is then removed to the water phase. The resultant reaction product of the cardenoxy polyether surfactant (CEO) can then be extracted into the organic solvent, from which it can be separated as a pale brown liquid. In certain embodiments in this regard, the etherifying step can provides a yield of cardenoxy polyether surfactant of about 85% to about 90%, or about 87.3%.

In other embodiments, the polyethylene glycol used in this step can have a varying molecular weight. By way of non-limiting example, the polyethylene glycol can have a molecular weight of about 450 to about 2000 g/mol.

In another embodiment of the present methods, in the grafting step, the cardenoxy polyether surfactant (CEO) can be mixed with the imidazole, trimethylamine (TEA), 4-dimethylaminopyridene (DMAP), dry dichloromethane (DCM) and methanesulfonyl chloride (MSC) to obtain the grafted CEO imidazole. In this regard, the CEO, TEA, and DMAP can be dissolved in the DCM, after which the MSC can be added to obtain a reaction mixture. In certain embodiments, the reaction mixture can be cooled to about 0° C. before the MSC is added, which can be done under nitrogen gas. This reaction mixture can then be stirred at room temperature for about 2 hours or longer.

In another embodiment, further DCM can then be added to the reaction mixture to obtain a diluted reaction mixture. In certain embodiments, the diluted reaction mixture can be washed with one or more of water and a brine solution and can be dried over anhydrous $MgSO_4$ and then concentrated. In other embodiments, this reaction mixture can then be heated with imidazole and chlorobenzoic acid, with or without a solvent, under nitrogen gas. These steps can occur, for example, at a temperature of about 55° C. to about 85° C., about 60° C. to about 80 °C, or about 70° C. The reaction mixture can then be purified to obtain the grafted CEO imidazole. Such purification can be done, by way of non-limiting example, by silica gel chromatography to provide the grafted CEO imidazole.

In a further embodiment, the quaternizing step can be conducted by mixing the grafted CEO imidazole with an alkyl halide followed by removing residual solvent. By way of non-limiting example, the alkyl halide can be an alkyl bromide, such as 1-bromopropane. This quaternizing step can be conducted, for example, under nitrogen atmosphere and heating for about 7 hours or more, and at a temperature of about 65° C. to about 95° C., about 70° C. to about 90 °C, or about 80 °C. As a result, the method can provide an about 90% to about 95% yield, or an about 92.8% yield, of the cardenyl polyethoxy imidazolium ionic liquid (CEOIm) as a viscous brown liquid.

This process for obtaining a cardenyl polyethoxy imidazolium ionic liquid (CEOIm) can be summarized by referring to the following reaction scheme:

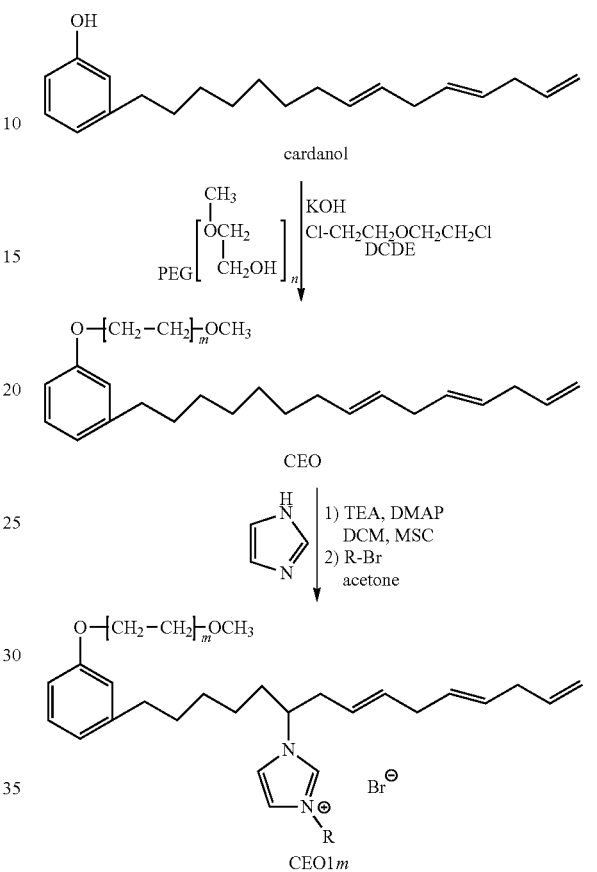

In one embodiment, the present subject matter relates to a cardenyl polyethoxy imidazolium ionic liquid (CEOIm) prepared according to the methods described above.

In another embodiment, the present subject matter relates to a method for preparing a dicardenoxy imidazolium ionic liquid (DCIm), the method comprising: obtaining cardanol extracted from cashew nut oil; dissolving the cardanol in a mixture of epichlorhydrin and water to obtain CGE having the formula:

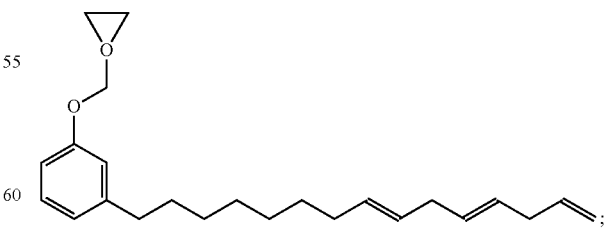

mixing the CGE with a compound of the formula $H_2N$—$(-CH_2-CH_2-NH)_n$—H, wherein n is an integer between 3 and 5, to obtain a cardanol amine (CIm) having the formula:

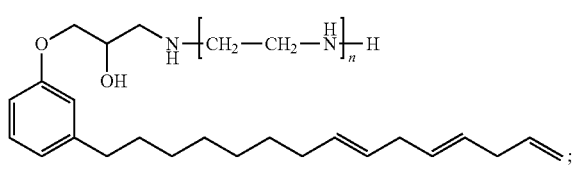

dissolving the CIm in acetic acid or trifluoroacetic acid to obtain an amine solution; and adding an aldehyde solution to the amine solution to obtain the dicardenoxy imidazolium ionic liquid (DCIm).

In one embodiment of the present methods of obtaining a dicardenoxy imidazolium ionic liquid (DCIm), the dicardenoxy imidazolium ionic liquid (DCIm) can be 1,3-bis(2-((2-hydroxy-3-(3-((8E,11E)-pentadeca-8,11,14-trien-1-yl)phenoxy)propyl)amino)ethyl)-1Himidazol-3-ium-2-ide acetate.

In certain embodiments of making the dicardenoxy imidazolium ionic liquid (DCIm) in this regard, the cardanol can be dissolved in the mixture of epichlorohydrin and water at a molar ratio of about 1:2 of cardanol to epichlorohydrin. This reaction mixture can be heated until the epichlorohydrin begins to boil. At that point, the heating can stop and caustic soda can be added stepwise under refluxing, for example, for about 1 hour, until the reaction mixture becomes viscous. Any excess epichlorohydrin can then be removed, for example, by vacuum distillation. The remaining mixture can then be dissolved, for example, in chloroform, which can again be removed by vacuum distillation to obtain the CGE.

In other embodiments of making the dicardenoxy imidazolium ionic liquid (DCIm), the compound of the formula H2N—(—CH$_2$—CH$_2$—NH)$_n$—H can be selected from the group consisting of triethylene tetramine (TETA), tetraethylenepentamine (TEPA), and penaethylenehexamine (PEHA). Once this component is mixed in, any excess amine can be removed, for example, by brine extraction, at which point the organic phase can be evaporated to obtain the CIm as a viscous red oil.

In certain embodiments of the final step of this process, the aldehyde solution can be prepared by dissolving glyoxal monohydrate with formaldehyde in an acetic acid or trifluoroacetic acid aqueous solution. Once separately prepared, the aldehyde solution can be added to the amine solution, for example, under stirring for about 5 hours or more and, for example, at a temperature of about 65° C. to about 95° C., about 70° C. to about 90° C., or about 80 °C. The resultant DCIm can then be obtained as a viscous liquid after all solvents are evaporated, for example, under vacuum.

This process for obtaining a dicardenoxy imidazolium ionic liquid (DCIm) can be summarized by referring to the following reaction scheme:

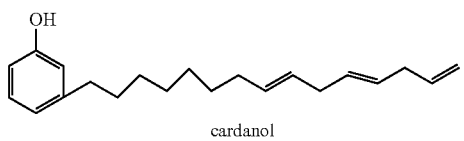

cardanol

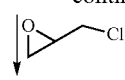

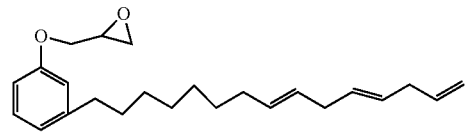

CGE

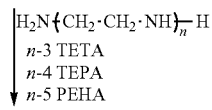

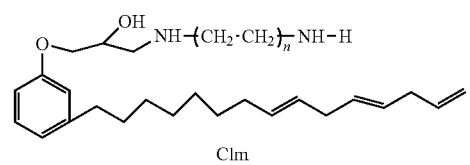

CIm

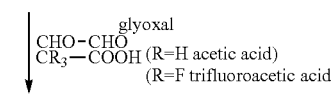

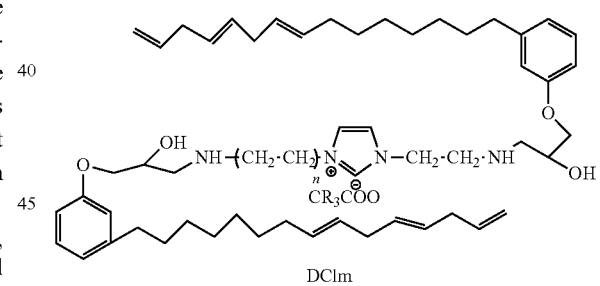

DCIm

In one embodiment, the present subject matter relates to a dicardenoxy imidazolium ionic liquid (DCIm) prepared according to the methods described herein.

In a further embodiment, the present subject matter relates to a method for preparing a dicardnyl tri-imidazolium ionic liquid (DCTIm), the method comprising: heating the dicardenoxy imidazolium ionic liquid (DCIm) prepared herein with an alkyl halide; and obtaining the dicardnyl tri-imidazolium ionic liquid (DCTIm). In certain embodiments, the alkyl halide can be an alkyl bromide, such as, by way of non-limiting example, 1-bromopropane. This process can result in a dicardnyl tri-imidazolium ionic liquid obtained as a viscous brown liquid.

This process for obtaining a dicardnyl tri-imidazolium ionic liquid (DCTIm) can be summarized by referring to the following reaction scheme:

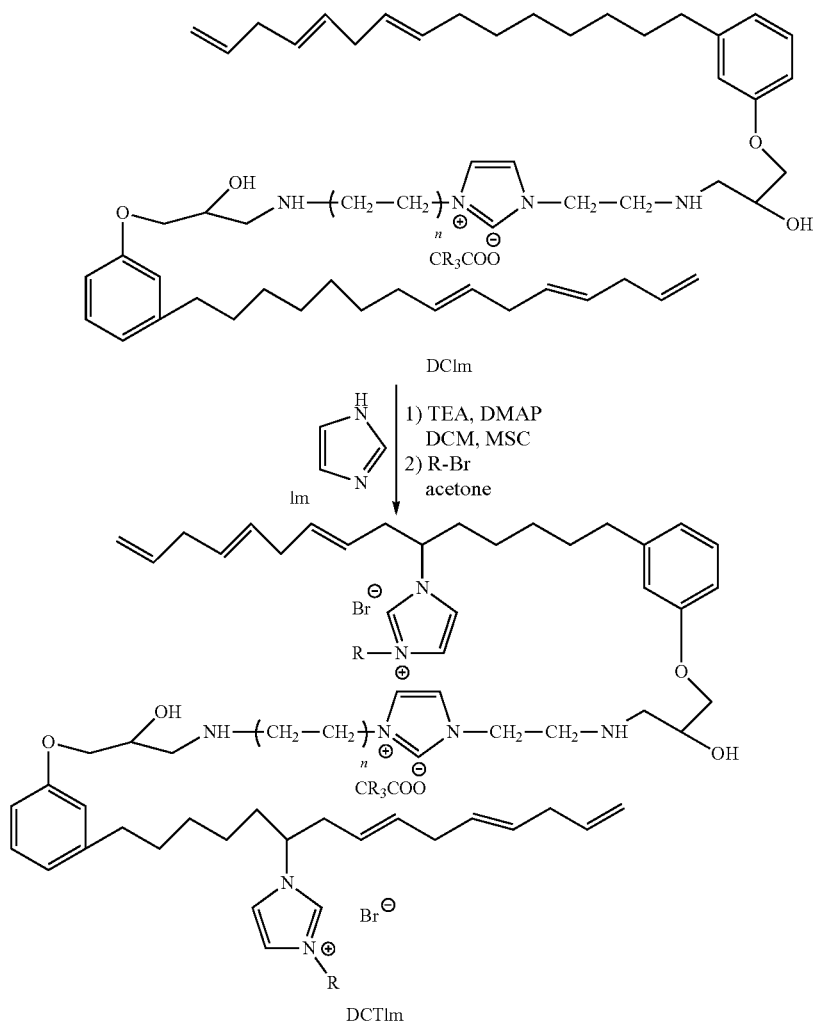

DCTlm

R = CH3, C2H5, C3H7, C4H9,
C5H11, C6H13, C7H15, C12H26

In one embodiment, the present subject matter relates to a dicardnyl tri-imidazolium ionic liquid (DCTIm) prepared according to the methods described herein.

In one more embodiment, the present subject matter relates to a method for preparing nanoparticles modified by a cardanol imidazolium ionic liquid, the method comprising: contacting nanoparticles of a substance of interest with the cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof; and obtaining the modified nanoparticles, wherein the substance of interest is selected from the group consisting of magnetite, calcium carbonate, and silica.

In yet another embodiment, the present subject matter relates to a method of preparing magnetite nanoparticles capped with a cardanol imidazolium ionic liquid, the method comprising: stirring magnetite in water; adding $NH_4OH$ to the magnetite in water to obtain a pH of about 10; adding oleic acid to obtain a ferrofluid; adding a solution of the cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in dichloromethane and ethanol with subsequent adding of an excess of ferrofluid to obtain a magnetic hybrid capped with the oleic acid as an inner layer and the cardanyl imidazolium ionic liquid as an outer layer; and separating the capped magnetic hybrid by using a magnet.

In certain embodiments of these methods for preparing the magnetic nanoparticles capped with a cardanol imidazolium ionic liquid, the capped magnetic hybrid can be selected from the group consisting of $Fe_3O_4$@OA/CEOIm; $Fe_3O_4$@OA/DCIm; $Fe_3O_4$@OA/DCTIm; and combinations thereof.

In one embodiment, the present subject matter relates to magnetite nanoparticles capped with a cardanol imidazolium ionic liquid prepared according to the methods described herein. In this regard, these magnetite nanoparticles can have an inner layer of oleic acid and an outer layer of the cardanol imidazolium ionic liquid.

In still yet another embodiment, the present subject matter relates to a method of preparing modified calcium carbonate nanoparticles, the method comprising: preparing an aqueous solution of calcium carbonate (Ca(OH)$_2$) in water; adding a solution of a cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in ethanol to the aqueous solution of calcium carbonate to obtain a reaction solution; adding CO$_2$ bubbles through the reaction solution until the reaction solution reaches a pH of about 7; and separating the modified calcium carbonate nanoparticles by centrifugation, wherein the modified calcium carbonate nanoparticles are selected from the group consisting of CaCO$_3$/CEOIm, CaCO$_3$/DCIm, CaCO$_3$/DCTIm, and combinations thereof. In this regard, the solution of the cardanyl imidazolium ionic liquid in ethanol can be added dropwise to the calcium carbonate.

In another embodiment in this regard, the CO$_2$ bubbles can be produced by heating ammonium bicarbonate in a closed flask, which is then connected to the reaction flask to produce the CO$_2$ bubbles. In another embodiment, the separation can be performed by centrifugation at a speed of about 10000 rpm for about 30 minutes or more. The resultant nanomaterials can be washed with, e.g., ethanol before undergoing further separation by an ultracentrifuge.

In one embodiment, the present subject matter relates to modified calcium carbonate nanoparticles prepared according to the methods described herein.

In one more embodiment, the present subject matter relates to a method of preparing functionalized silica nanoparticles, the method comprising: aging silica (SiO$_2$) nanoparticles with a solution of a cardanyl imidazolium ionic liquid selected from the group consisting of a cardenyl polyethoxy imidazolium ionic liquid (CEOIm), a dicardenoxy imidazolium ionic liquid (DCIm), a dicardnyl tri-imidazolium ionic liquid (DCTIm), and a combination thereof in toluene, whereby the cardanyl imidazolium ionic liquid diffuses and adsorbs on a surface of the silica nanoparticles; decanting supernatant and collecting the functionalized silica nanoparticles; and separating the functionalized silica nanoparticles by centrifugation.

In one embodiment, the present subject matter relates to functionalized silica nanoparticles prepared according to the methods described herein.

In a further embodiment, the present subject matter relates to a method for dispersing oil spilled on seawater, the method comprising: applying the nanoparticles modified by a cardanol imidazolium ionic liquid prepared according to the present methods to seawater having the oil spilled thereon; and dispersing the oil spilled on the seawater.

According to this embodiment, the imidazolium ionic liquids, and the resultant nanoparticles, produced herein can be used as oil spill dispersants. For example, application of the present imidazolium ionic liquids, and the resultant nanoparticles, can be added to heavy crude oil spilled on the surface of sea water to disperse and extract the heavy crude oil. In this regard, the present IILs or their corresponding nanoparticles can be added to the oil spill at different ratios from 1:1 to 1:100. The resultant dispersion of crude oil in sea water can then be removed, and the crude oil extracted using chloroform, for example. Once the chloroform is evaporated, the weight of the extracted crude oil can be determined, and the oil spill collection efficiency (OCE) can be calculated using the following formula:

$$OCE = \frac{\text{Wt. of extracted crude oil} \times 500}{\text{Wt of crude oil}} \quad (1)$$

In another embodiment, the present subject matter relates to a method for collecting spilled oil, the method comprising: applying the nanoparticles comprising magnetite nanoparticles capped with a cardanol imidazolium ionic liquid prepared according to the present methods to spilled oil; and collecting the spilled oil.

In further embodiments, the various capped magnetite nanoparticles prepared herein are useful as oil spill collectors for heavy crude oil. In this regard, the magnetic materials based on Fe$_3$O$_4$@CEO, Fe$_3$O$_4$@CEOIm, Fe$_3$O$_4$@CIm, Fe$_3$O$_4$@DCEIm, and Fe$_3$O$_4$@DCTIm can be used as oil spill collectors for heavy crude oil, using magnetic cardanol to oil ratios (MOR) of from about 1:1 to about 1:100.

In this regard, not only can the present magnetite nanoparticles capped with a cardanol imidazolium ionic liquid be used for collecting spilled oil, but they can be reused multiple times to collect the spilled oil. In this regard, the present magnetite nanoparticles capped with a cardanol imidazolium ionic liquid can be used, 2, 3, 4, or more times to collect the spilled oil.

In still another embodiment, the present subject matter relates to a method for reducing viscosity of heavy crude oil, the method comprising: applying the nanoparticles modified by a cardanol imidazolium ionic liquid prepared according to the present methods to heavy crude oil, thereby reducing the viscosity of the heavy crude oil.

In further embodiments in this regard, the present nanoparticles modified by a cardanol imidazolium ionic liquid can be used to improve the viscosity of heavy crude oil, thereby improving their ability to disperse asphaltenes. Moreover, their ability to reduce interfacial tension, and wettability of, e.g., sandstone and calcite rock, make these present materials suitable for application in the field of heavy crude oil enhanced recovery.

In one more embodiment, the present subject matter relates to a method for enhancing recovery of crude oil spilled on rock, the method comprising: applying the nanoparticles modified by a cardanol imidazolium ionic liquid prepared according to the present methods to rock having the crude oil spilled thereon; and recovering the crude oil spilled on the rock. Non-limiting examples of rocks to which the present materials can be applied include sandstone and calcite rock.

EXAMPLES

Materials

The chemicals used to modify the chemical structure of cardanol to produce imidazolium ionic liquids as used and described herein were purchased from Sigma-Aldrich Chemicals Co., USA. Cardanol extracted from Cashew nut oil was obtained from Shanghai Judong Trading Company Ltd., China. Imidazole, β,β-dicholorodiethylether (DCDE), epichlorohydrine (ECH), and sodium hydroxide were used to prepare the cardanoxy surfactant. Ethylene glycol (EG), diethylene glycol (DEG), triethylene glycol (TEG), tetraethylene glycol (TTG) and polyethylene glycols (having different molecular weights ranging from 450 to 2000 g/mol) monomethyl ether were used to etherify cardanol. Ethylene diamine (EDA), diethylene triamine (DETA), triethylene tetramine (TETA) and pentaethylene hexamine (PEHA) were used as polyamines to aminate the cardanol. Acetic acid, trifluoroacetic acid, glyoxal monohydrate and formaldehyde were used to condense cardanoxy polyamines to imidazolium ionic liquids. Triethylene amine (TEA), 4-dimethylaminopyridene (DMAP), and methanesulfonyl chloride were used as reagents to graft imidazole on hydrophobic parts of cardanol. Alkyl bromides having different alkyl chains ranging from methyl to octadecyl bromide were used to quaternize cardanoxy grafted imidazole. Solvents such as toluene, heptane, xylene and isooctane were used in both synthesis and evaluation of the prepared PIL respectively.

Heavy Arabic crude oil (20.8° API), having specific gravity, water, wax and asphaltene contents of 0.929 g/cm$^3$, 0.145 wt %, 2.3 wt % and 8.3 wt %, respectively, was produced from Ras Tanura wells by Aramco, Saudi Arabia. Its asphaltene fractions were precipitated from the crude oil using a toluene:n-heptane solvent as a precipitant with a volume ratio of 1:40 based on ASTM D2007. Its molecular weight as determined by gel permeation chromatography (GPC) was 6350 g/mol. The sea water was collected from the Arabic Gulf and used to prepare synthetic crude oil emulsions having different crude oil/water compositions (90/10, 70/30 and 50/50 volume %).

Fresh Berea sandstone samples were used for the different flooding runs. Routine core analysis was conducted on the tested samples and their petrophysical properties are listed in Table 1.

TABLE 1

Petrophysical properties of Berea sandstone rocks

| Core sample | Length, cm | Diameter, cm | Porosity, % | Permeability, md |
|---|---|---|---|---|
| 1 | 5.2 | 3.8 | 0.22 | 183.6 |
| 2 | 4.9 | 3.8 | 0.21 | 303.6 |
| 3 | 5.0 | 3.8 | 0.20 | 293.2 |

Heavy and medium Saudi crude oil was provided from Ras Tanura oil field, Aramco, Saudi Arabia.

Iceland spar (CaCO$_3$, Ward's Natural Science) was used as a model surface. Prior to treatment, calcite crystals were cleaved carefully into approximately 1×2 cm pieces with smooth surfaces. Care was taken to handle calcite samples only by their edges so that the freshly cleaved surfaces were not contaminated. All the samples were soaked in de-ionized distilled water in a container that was shaken in an ultrasonic bath for a few minutes to remove debris from the surfaces. Each sample then was removed from the container, rinsed with distilled water, put into a new container, and aged in de-ionized water again. This procedure was repeated several times until the water remained clear.

Characterization of Cardanyl Imidazolium ILs and their Nanoparticles

The chemical structures of the prepared cardanyl imidazolium ILs and their nanoparticles were determined from Fourier Transform Infrared (FTIR; Nicolet 6700 spectrometer using KBr pellets), $^1$H and $^{13}$C nuclear magnetic resonance (NMR; AVANCE 400 Bruker spectrometer using deuterated dimethyl sulfoxide as the solvent).

Thermal characteristics of cardanyl imidazolium ILs and their nanoparticles were evaluated by differential scanning calorimetry (DSC; Shimadzu DTG-60M) and conducted under nitrogen atmosphere at a heating rate of 10° C. per minute.

A polarized optical microscope (Olympus BX-51 microscope attached with a 100 W mercury lamp) was used to determine the size and shape of the crude oil/seawater emulsions.

Surface Tension, Interfacial Tension (IFT) and Contact Angle were determined based on pendant drop technique using drop shape analyzer model DSA-100 (Kruss GmbH, Hamburg, Germany). This instrument was monitored with a digital camera. Young-Laplace equation was employed to calculate the contact angle with analysis software DSA4 software (V.1.0-03). Pendent drops were formed on the tip of a Teflon capillary with an outside and inside diameter of 0.1 and 0.076, respectively.

The IFT and contact angle at reservoir conditions (600° C. and 2000 psi) were determined using another pendant drop shape tensiometer (model Temco IFT-10). The instrument was composed of high-pressure cell, hand pump for fluids displacement, vibration-free table, needle, temperature controller, pressure transducer, back pressure regulator, lamb, digital camera supplied with video frame grabber for image. IFT is measured by upward injection of drop of oil to the tip of proper size needle immersed in seawater or synthesized PILs solutions. Contact angle between crude oil and synthesized PILs solutions on rock surface at reservoir conditions (600° C. and 2000 psi) was measured using the same setup with some modification.

Example 1

This method was based on the etherification of cardanol with PEG having different molecular weights followed by grafting and quaternization of imidazole to prepare cardenyl polyethoxy imidazolium ionic liquids (CEOIm). In this respect, preparation method of 1-((8E,11E)-1-(3-(2-hydroxyethoxy)phenyl)pentadeca-8,11,14-trien-6-yl)-3-propyl-1H-imidazol-3-ium bromide was reported as representative for (CEOIm) ILs. Cardanol (0.1 mol) was mixed with PEG (0.1 mol), DCDE (0.1 mol), toluene (50 mL), and NaOH pellets (0.2 mol). The reaction temperature was increased up to 120° C. with stirring the reaction mixture under N$_2$ atmosphere for 6 h. The produced NaCl precipitate and the unreacted NaOH were separated from the reaction by filtration. Toluene solvent and the unreacted DCDE were evaporated from the reaction filtrate under pressure using rotary evaporator. The reaction product was mixed with 20 mL of isopropanol and hot aqueous solution of saturated NaCl to salt out the unreacted PEG to water phase. The reaction product was extracted into organic solvent using separatory funnel. The cardanoxy polyether surfactant was designated as CEO and separated as pale brown liquid with reaction yield of 87.3%.

The purified CEO (0.032 mol), trimethylamine (TEA; 0.041 mol), and DMAP (0.003 mol) were dissolved in dry dichloromethane (DCM; 150 mL) and cooled to zero degrees, then methane sulfonyl chloride (0.033 mol) was added slowly under nitrogen gas and stirred at room temperature for 2 h. The reaction mixture was diluted with DCM, washed with water, brine solution, dried over anhydrous MgSO$_4$, and then concentrated. The product was heated with imidazole (0.1 mol) and chloroperbenzoic acid (0.1 mol) without solvent at 70° C. under N$_2$ atmosphere and then purified by silica gel column chromatography (2% methanol in DCM) to provide grafted CEO imidazole. After that, alkyl bromide such as 1-bromopropane (0.1 mol) was added to CEO imidazole, stirred and heated for 7 h at 80° C. and protected with nitrogen. The viscous brown liquid was produced, and it was washed several times with distilled water. Residual solvent was removed under reduced pressure, yielding 92.8% of 1-((8E,11E)-1-(3-(2-hydroxyethoxy)phenyl)pentadeca-8,11,14-trien-6-yl)-3-propyl-1H-imidazol-3-ium bromide as a representative sample of CEOIm.

Example 2

The second method is based on preparation of dicardnoxy imidazolium ionic liquids (DCIm). As an example, 1,3-bis (2-((2-hydroxy-3-(3-(((8E,11E)-pentadeca-8,11,14-trien-1-yl)phenoxy)propyl)amino)ethyl)-1Himidazol-3-ium-2-ide acetate was represented. In this respect, cardanol (1 mol) was dissolved in a mixture of an excess of epichlorohydrin (2 mol) and 20 ml water in a three-necked flask. The reaction mixture was heated until epichlorohydrin began to boil. After the heating stopped, caustic soda (1 mol) was added in portions and the reaction mixture was refluxed for 1 h until it become viscous. The excess epichlorohydrin was removed by vacuum distillation. The remaining mixture was dissolved in chloroform and the precipitated sodium chloride was removed by filtration. The product was obtained after removing chloroform via vacuum distillation to prepare CGE. Typically, 3.26 g (9 mmol) of CGE in 50 mL $CHCl_3$ was added to 6.4 g (27 mmol) of penaethylenehexamine (PEHA) in 10 mL $CHCl_3$ and the mixture was refluxed overnight. The excess of amine was removed by brine extraction (50 mg/L). The organic phase was evaporated to obtain viscous red oil as CIm. Cardanol amine (CIm; 3.4 mmol) was dissolved in 50 mL of (50 volume % acetic acid) aqueous solution to prepare the amine solution. Glyoxal monohydrate (1.7 mmol; 129 mg) was dissolved with formaldehyde (0.05 mol; 134 μl) in 50 mL of acetic acid aqueous solution (50 volume %) in a separate flask. The aldehyde solution was added to the amine solution under vigorous stirring and heated at 80° C. for 5 h. The DCIm was obtained as a viscous liquid after evaporation of all solvents under vacuum using a rotary evaporator system.

Example 3

This method was used to prepare dicardnyl tri-imidazolium ILs (DCTIm). In this respect, DCIm (0.1 mol; Scheme 2) was heated with alkyl bromide such as 1-bromopropane (0.2 mol), stirred and heated for 7 h at 80° C., under nitrogen atmosphere. The viscous brown liquid was produced and washed several times with distilled water. The product of DCTIm was evaporated under reduced pressure using rotary evaporator system to obtain viscous brown DCTIm as the ILs.

Example 4

Magnetic nanoparticles capped with cardanol imidazolium ILs were prepared by the capping of magnetite with inner and outer layers. The inner layer was of oleic acid, and the outer layer was of cardanyl imidazolium ionic liquids CEOIm, DCIm, and DCTIm, as prepared in examples 1, 2, and 3, respectively.

Initially, magnetite (125.0 mg) was subjected to mechanical stirring in 50 mL of Milli-Q water, then a few drops of $NH_4OH$ (30%) were added until a pH=10 was reached. Afterwards, 50 mL of oleic acid (OA) was further incorporated in the batch. The obtained ferrofluid was separated from the organic phase by magnetic attraction. The formation of the second passivation layer was performed through the addition of a solution of CEOIm, DCIm, or DCTIm (12.0 mg), dichloromethane (40 mL) and ethanol (60 mL) under sonication at 40° ° C. for 30 min, with subsequent addition of an excess of ferrofluid. The magnetic hybrid based on $Fe_3O_4$@OA/CEOIm; $Fe_3O_4$@OA/DCIm; or $Fe_3O_4$@OA/DCTIm was separated by using a magnet. This methodology was reproduced for the preparation of all nanomaterials described herein.

Example 5

An aqueous solution of $Ca(OH)_2$ (2 g) was vigorously stirred in 100 ml of deionized water (DIW) for 30 min in a flask fitted with a condenser, a dropping funnel, and a nitrogen inlet. Different concentrations (2-10 Wt %) of CEOIm, DCIm, or DCTIm were dissolved in 100 mL ethanol and then added dropwise to the $Ca(OH)_2$ solution with vigorous stirring. Ammonium bicarbonate was heated in a closed flask and connected to the reaction flask to produce $CO_2$ bubbles through the reaction solution until the pH of the solution reached 7. The calcium carbonate solutions underwent centrifugation at 10000 rpm for 30 min to separate the nanomaterials, which was washed several times with ethanol and separated with an ultracentrifuge. The modified $CaCO_3$ nanoparticles with CEOIm, DCIm, or DCTIm were designated as $CaCO_3$/CEOIm, $CaCO_3$/DCIm, and $CaCO_3$/DCTIm, respectively.

Example 6

Commercial $SiO_2$ nanoparticles were purchased from Sigma-Aldrich (St. Louis, MO, USA). Fresh silica nanoparticles were washed and posteriorly dried at 120° C. for 3 h. To enhance their surface functionality and hydrophobicity, the silica nanoparticles were aged using a solution of CEOIm, DCIm, or DCTIm in toluene at different concentrations (2-10 wt %) for two weeks at 25° C. and constant stirring at 200 rpm. During the aging process, diffusion and physical adsorption of the CEOIm, DCIm, or DCTIm occurred on the silica nanoparticle surface forming an egg-shell profile.

After the ageing process, the functionalized silica nanoparticles were collected after decanting the supernatant. After that, the nanoparticle functionalized with CEOIm, DCIm, or DCTIm were left to dry for a period of 6 h at 120° C. for eliminating any remaining solvent and allowing the dissolved CEOIm, DCIm, or DCTIm to transport throughout the silica surface. Then, the functionalized silica nanoparticles were washed with toluene several times. The resultant functionalized silica nanoparticles were left to dry at 25° C. until no change in mass was observed. The nanoparticles were separated by centrifugation.

Example 7

Characterization of Cardenyl Imidazolium ILs

The solubility of CEO and CEOIm prepared by Example 1 in water and toluene was increased with decreasing molecular weights of PEG used for etherification of phenol groups. It was also noticed that lowering the alkyl chain carbon number of the R groups of CEOIm (Scheme 1) increased its solubility in water and decreased its solubility in toluene. It was also noticed that the alkyl carbon number of CEOIm ranged from C5 to C8 increased its solubility in n-heptane. CEO was not solubilized into n-heptane even with lowering or increasing the molecular weights of PEG.

It was also noticed that the solubility of CIm, DCIm (Prepared by Example 2) and DCTIm (prepared by Example 3) were more solubilized in n-heptane with all polyamines used. Their solubility in water was increased with increases in the molecular weights of polyamines and lowering the carbon chain lengths attached to the imidazolium cations. Their solubility in toluene increased with increasing the carbon chain lengths attached to imidazolium cations (Examples 2 and 3).

Figure 2:
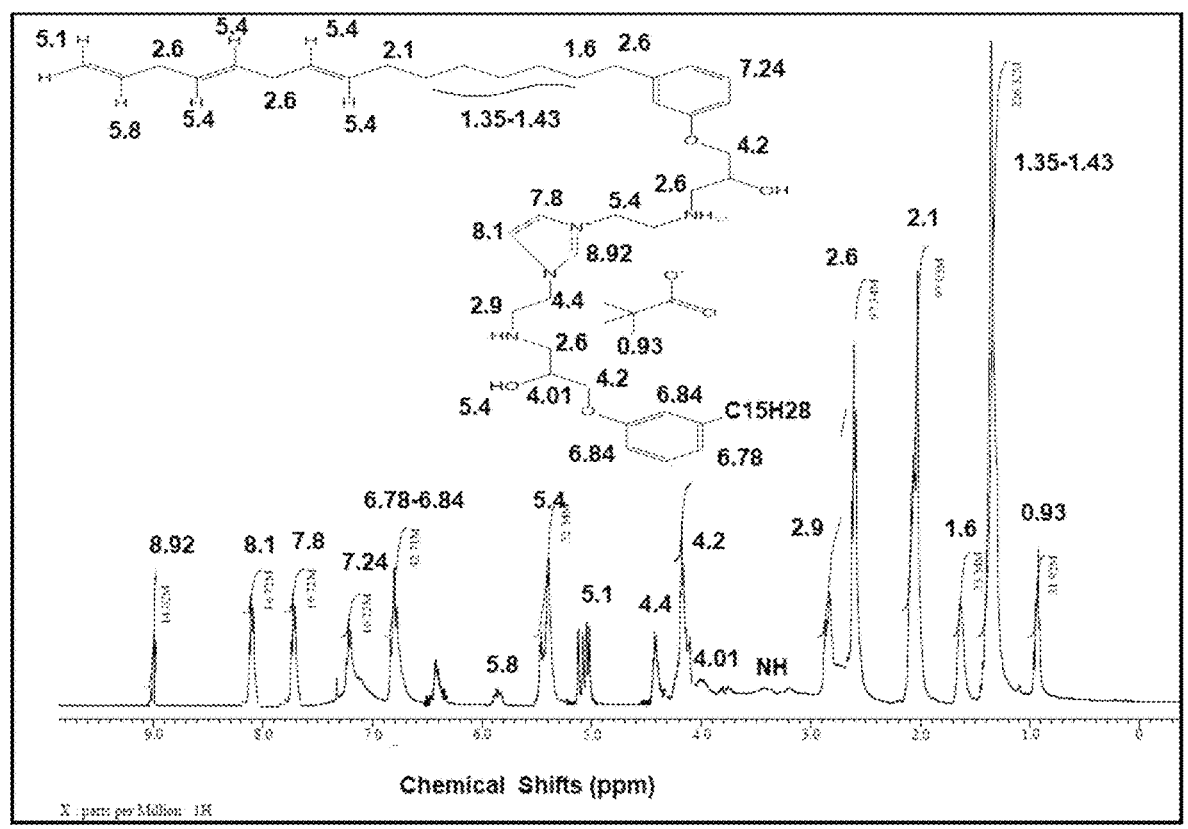
FIG. 2 is a $^1HNMR$ spectrum of DCIm.
Figure 3:
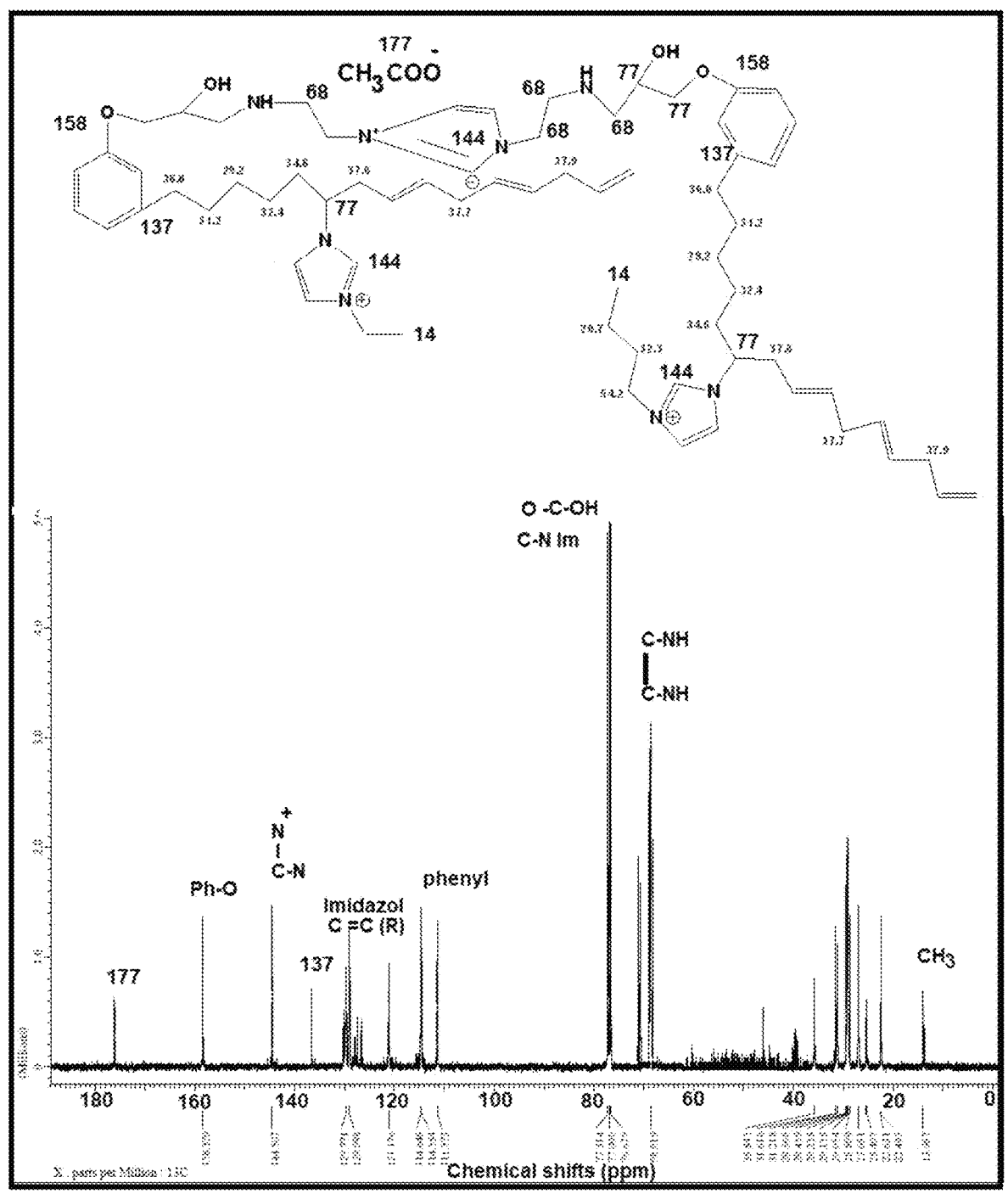
FIG. 3 is a $^{13}CNMR$ spectrum of DCTIm.

The chemical structures of CEOIm, DCIm, and DCTIm were confirmed from $^1HNMR$ and $^{13}CNMR$ spectra represented in FIG. 1-3. In this respect, the ethoxylation of the phenol group of cardanol to produce CEOIm was confirmed from the appearance of peaks at 3.69 and 4.33 ppm corresponding to ethoxy groups (FIG. 1). The alkylation of the grafted imidazole group in the chemical structure of CEOIm was elucidated from the peaks appearing at 8.92 and 7.92 ppm attributed to =CH—N+ of imidazole protons (FIG. 1). The same peak appeared in the 1HNMR spectrum of DCIm, represented in FIG. 2, to confirm the formation of imidazolium cations after the imidation of phenoxy groups and quaternization with alkyl bromide. The new peaks appeared at 4.2 and 4.4 ppm corresponding to N—$CH_2$—$CH_2$—N of polyamines elucidated the opening of glycidyl ether cardanol with polyamines via formation of imine groups to form DCIm. The presence of acetate or trifluoroacetate in the chemical structures of all prepared cardenyl imidazolium ILs (CEOIm, DCIm, and DCTIm) was elucidated from the appearance of peak at 177 ppm in 13CNMR spectra as DCTIm representative sample in FIG. 3. The grafting of imidazole of alkyl chain of cardanol was proved from the appearance of strong peaks at 78 ppm related to C—N imidazole and C—OH (FIG. 3).

Example 8

Characterization of Nanomaterials Capped with Cardenyl Imidazolium ILs

Figure 4A:
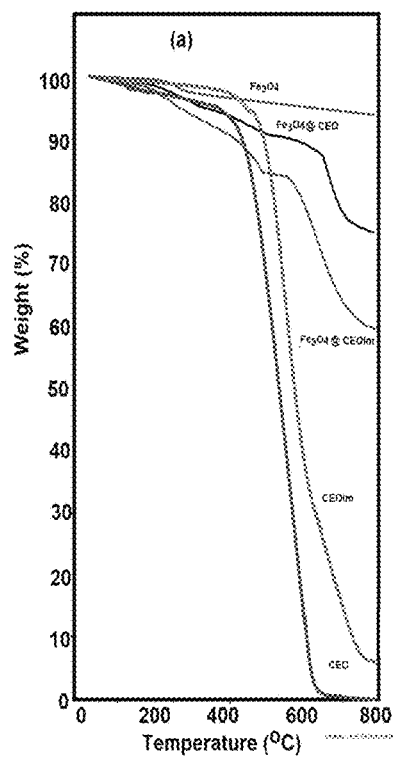
FIGS. 4A, 4B, and 4C shows TGA thermograms of magnetite nanoparticles coated with the present imidazolium ionic liquids.
Figure 4B:
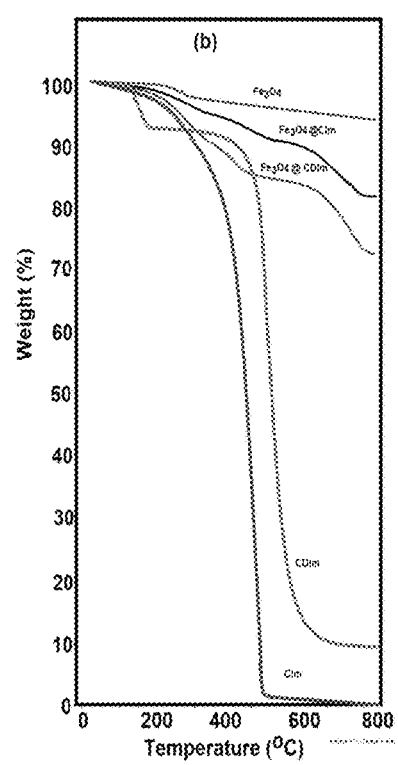
Figure 4C:
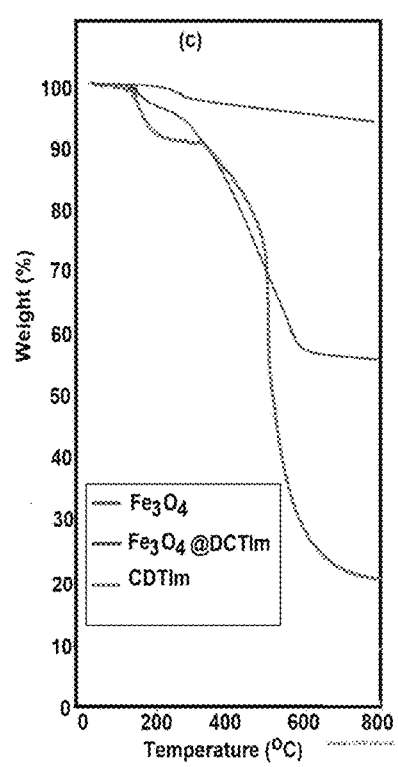

The thermal stability of CEOIm, DCIm, and DCTIm for thermal degradation was confirmed from TGA thermograms represented in FIGS. 4A-4C. It was noticed that CEOIm (prepared by Example 1; FIG. 4a) has a higher degradation stability that degraded at 480° C. The cardanyl imide ILs based on DCIm and DCTIm started the degradation at temperatures of 240 and 280° C., respectively (FIGS. 4B and 4C); this was referred to increase the basicity of imide ILs based on DCIm and DCTIm rather than CEOIm. The increasing of basicity decreased the thermal stability of the IILs. The remained residual contents (RS %) above 650° C. were increased in the order DCTIm>DCIm>CEOIm ILs, which reflect the remained char carbons and nitrogen cyclic thermal stable products. The RS % of DCTIm, DCIm, and CEOIm were 22, 14, 8 Wt %, respectively.

The effects of DCTIm, DCIm, CEOIm as capping agents for $Fe_3O_4$, $CaCO_3$ and $SiO_2$ nanoparticles (prepared by Examples 4-6) on their thermal stability was confirmed from TGA thermograms represented in FIGS. 4A, 4B, 4C, 5A, 5B, 5C, 6A, 6B, and 6C, respectively. The RS % values above 650° C. as compared with non-capped $Fe_3O_4$, $CaCO_3$, and $SiO_2$ nanoparticles (FIGS. 4-6A-C) were used to determine the percentages of DCTIm, DCIm, and CEOIm on the nanoparticles surfaces.

FIGS. 4A-4C elucidate that the magnetite lost approximately 6 wt. % from its original weight that referred to bonding of bound water and hydroxyl group at magnetite surfaces. The capping % of CEO and CEOIm on the magnetite surfaces of $Fe_3O_4$@CEO and $Fe_3O_4$@CEOIm (FIG. 4A) are 13 and 23 Wt. %, respectively, after excluding the lost weight of magnetite (5 wt. %) and RS % of ILs. This means that the ILs are more effective as capping agents than others. It was noticed also that the increasing of the imidazolium contents of DCTIm more than DCIm and CEOIm increased their capping percentages on all prepared nanoparticles.

Figure 5A:
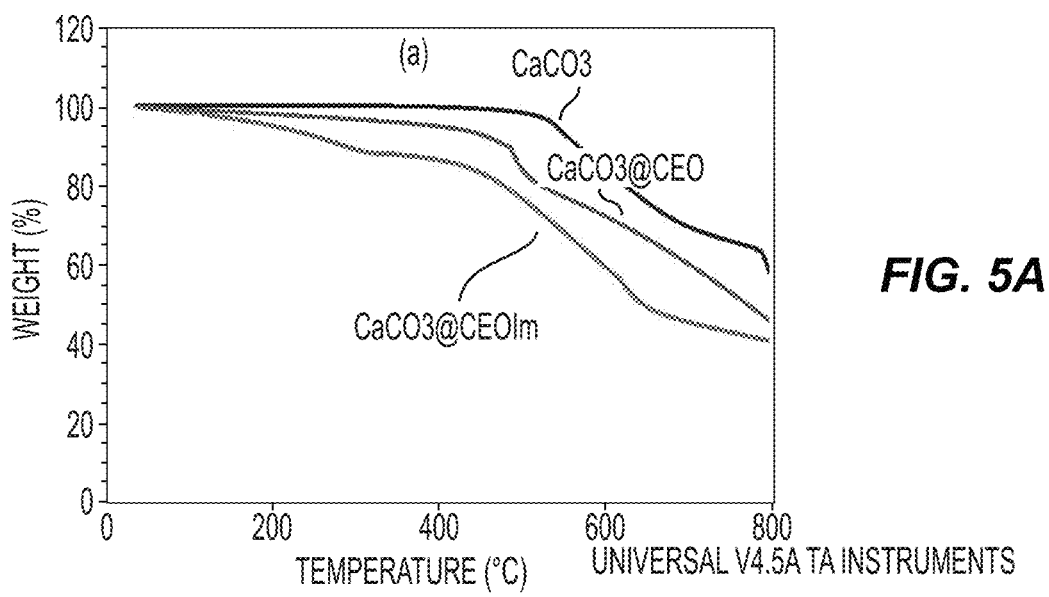
FIGS. 5A, 5B, and 5C shows TGA thermograms of calcium carbonate nanoparticles coated with the present imidazolium ionic liquids.
Figure 5B:
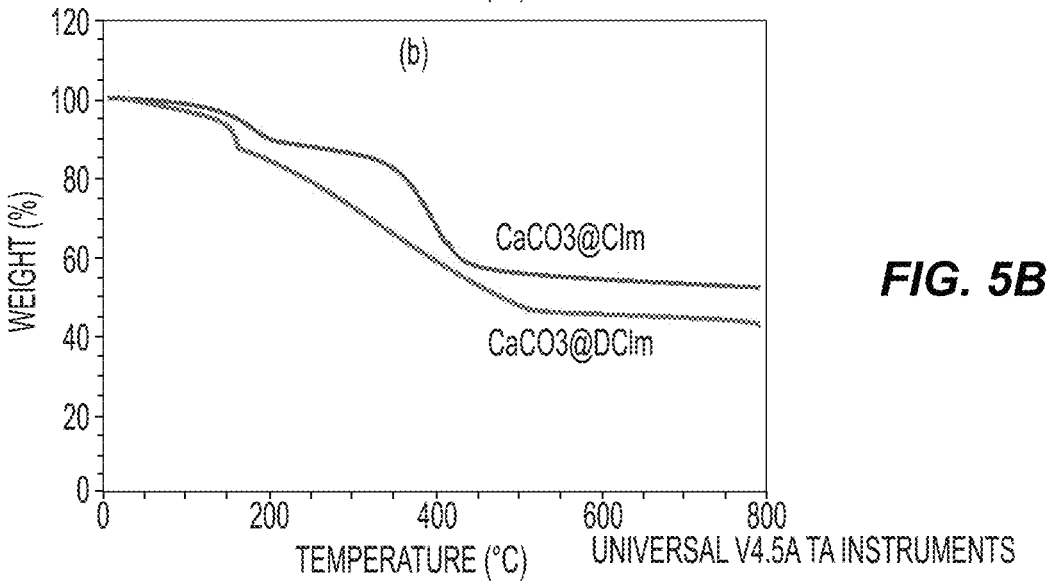
Figure 5C:
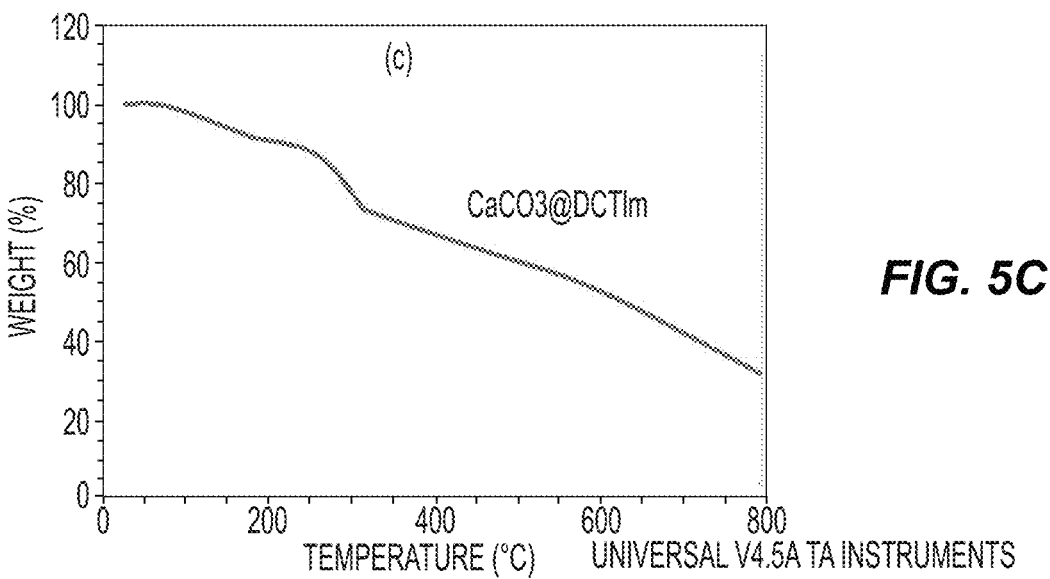

FIGS. 5A-5C show thermogravimetric analysis curves of $CaCO_3$, $CaCO_3$@CEO, $CaCO_3$@CEOIm, $CaCO_3$@CIm, $CaCO_3$@DCIm, and $CaCO_3$@DCTIm particles synthesized by Example 5. The TGA thermograms of $CaCO_3$ particles exhibited similar profiles and revealed that the decomposition occurs in two steps. The first step starts at 110° C. due to the loss of adsorbed water accounting for circa 2% of the initial mass. The second weight loss began to occur at the decomposition temperature of 552° C. to finish at about 740° C., which can be attributed to the thermal decomposition of $CaCO_3$ to CaO and $CO_2$. Essentially, the loss evaluated at 46-48% of the initial mass is attributed to the $CO_2$ escaping from the system after $CaCO_3$ decomposition. The same discussion on the capping percentages of DCTIm, DCIm, and CEOIm agree with that obtained with magnetite.

Figure 6A:
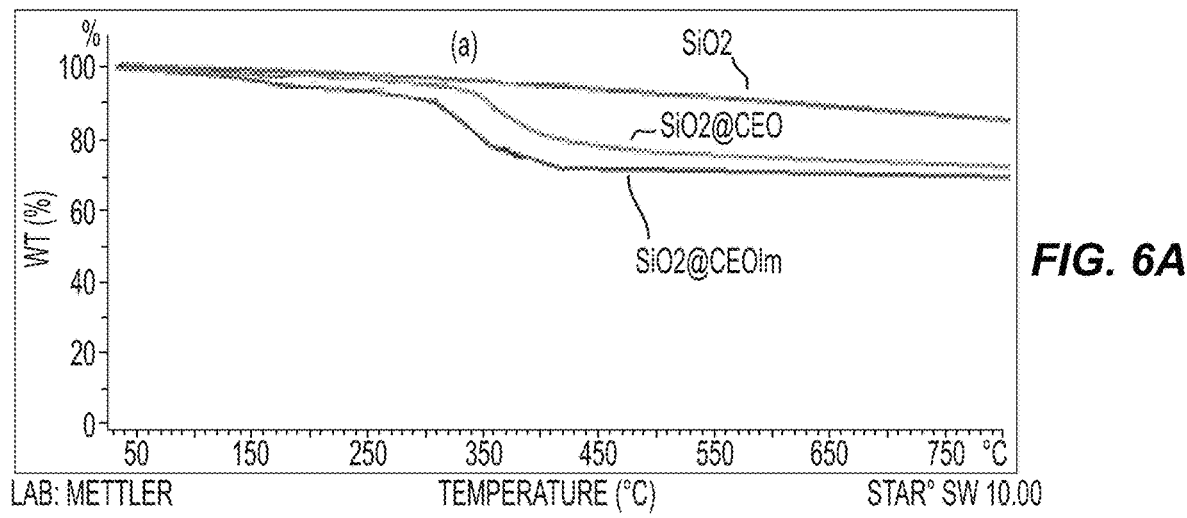
FIGS. 6A, 6B, and 6C shows TGA thermograms of silica nanoparticles coated with the present imidazolium ionic liquids.
Figure 6B:
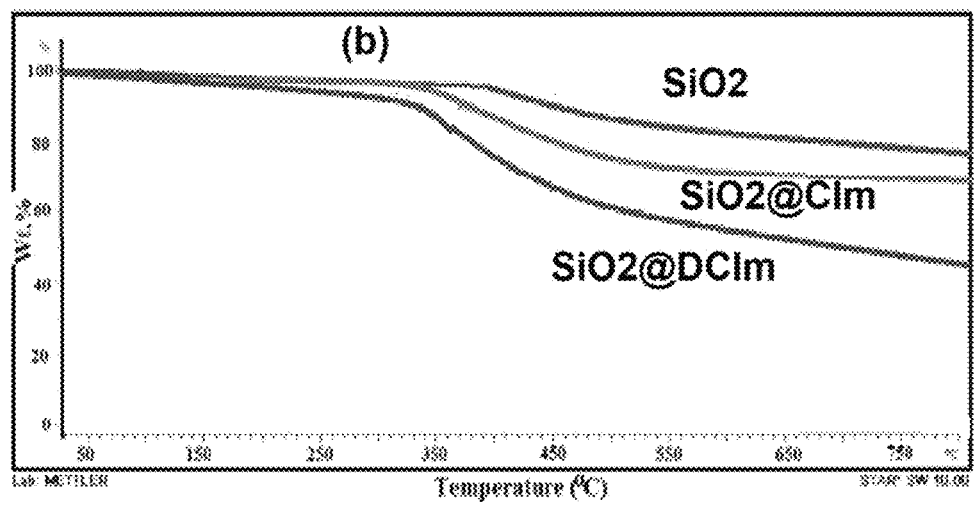
Figure 6C:
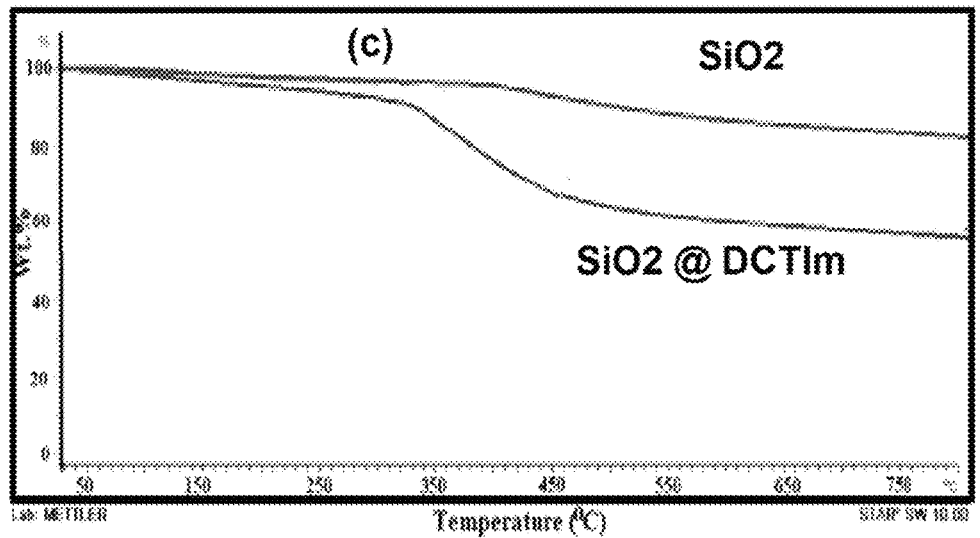
Figure 7A:
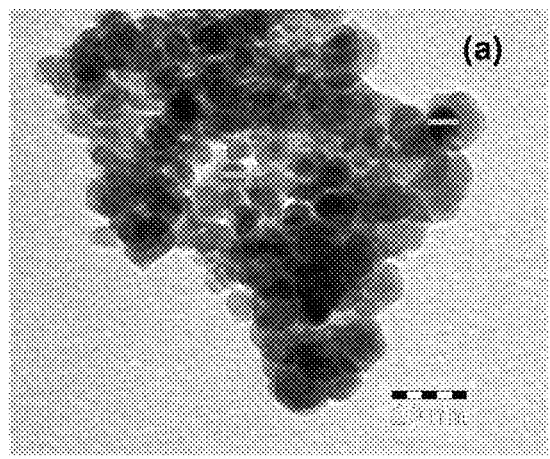
FIGS. 7A, 7B, 7C, and 7D show TEM micrographs of magnetite nanoparticles and their compositions with the present imidazolium ionic liquids.
Figure 7B:
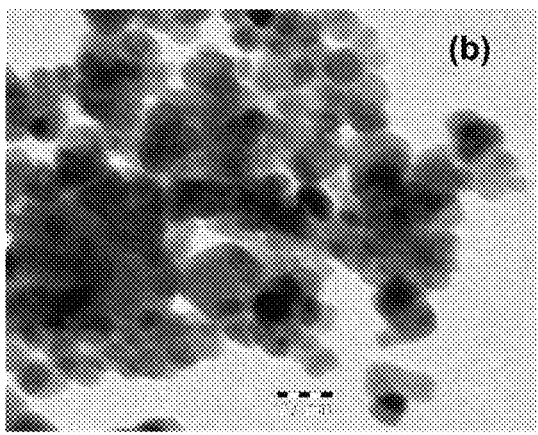
Figure 7C:
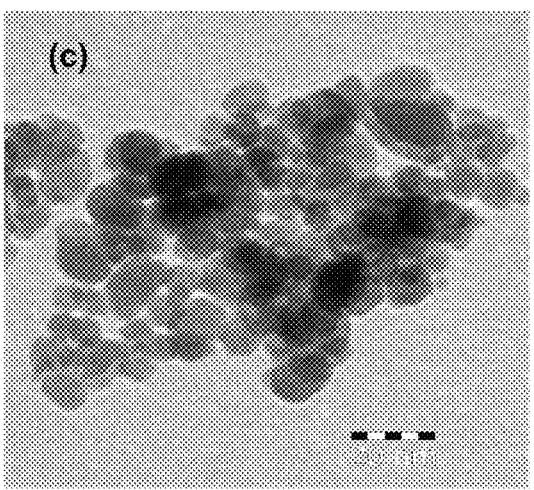
Figure 7D:
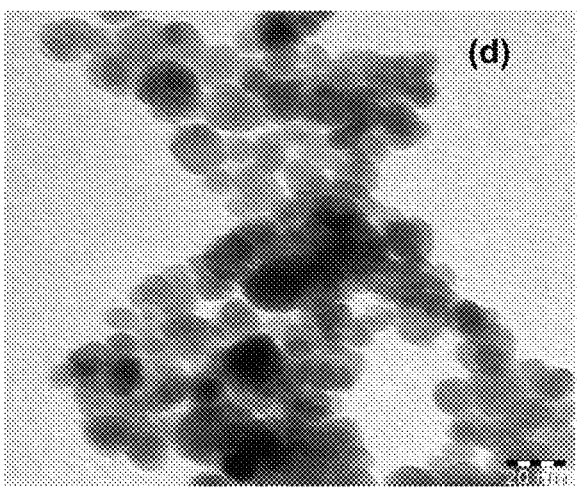
Figure 8A:
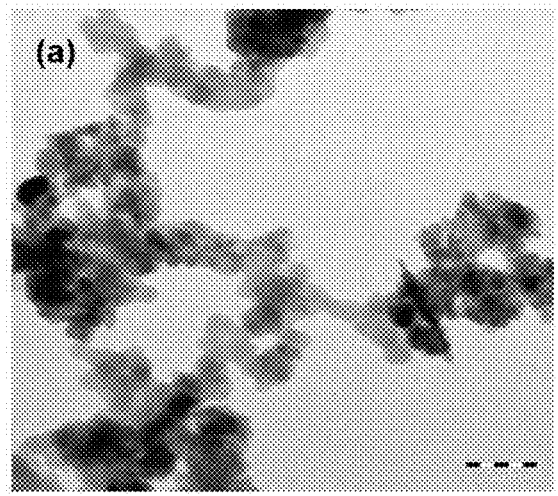
FIGS. 8A, 8B, 8C, and 8D show TEM micrographs of calcium carbonate nanoparticles and their compositions with the present imidazolium ionic liquids.
Figure 8B:
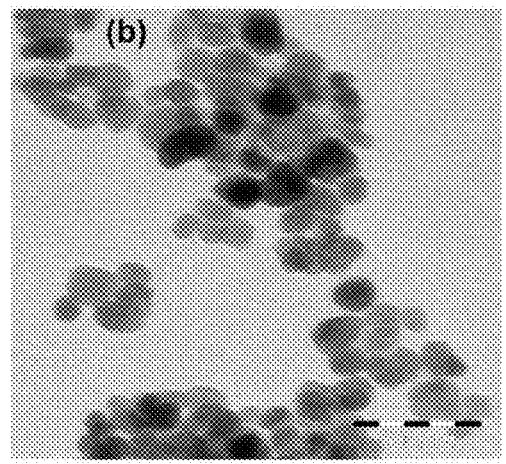
Figure 8C:
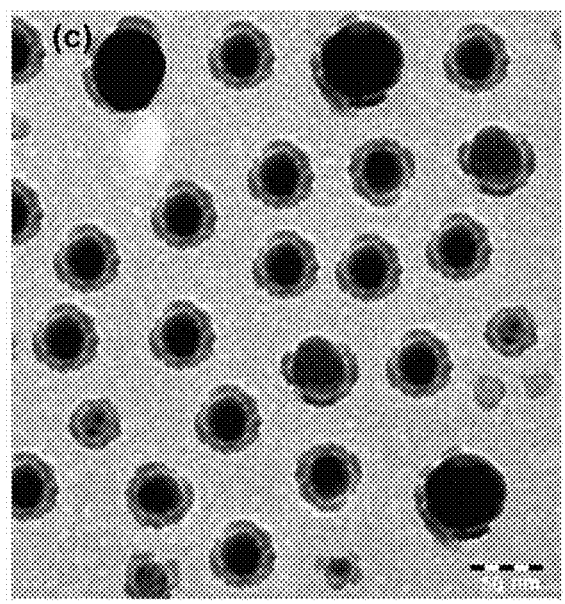
Figure 8D:
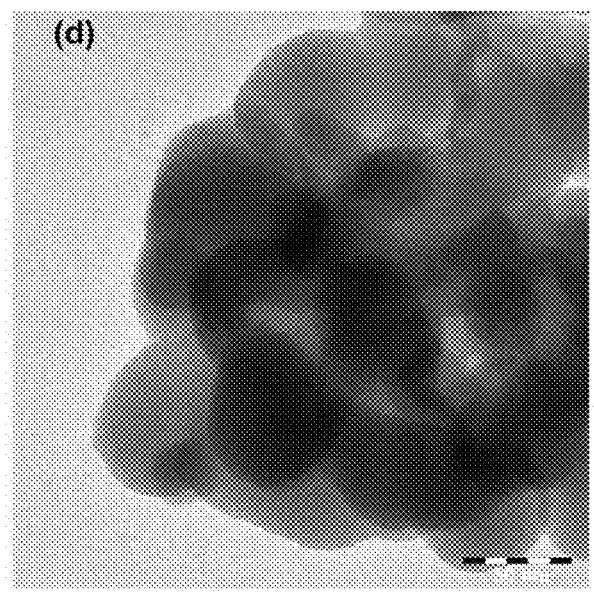
Figures 9A, 9B, 9C, 9D:
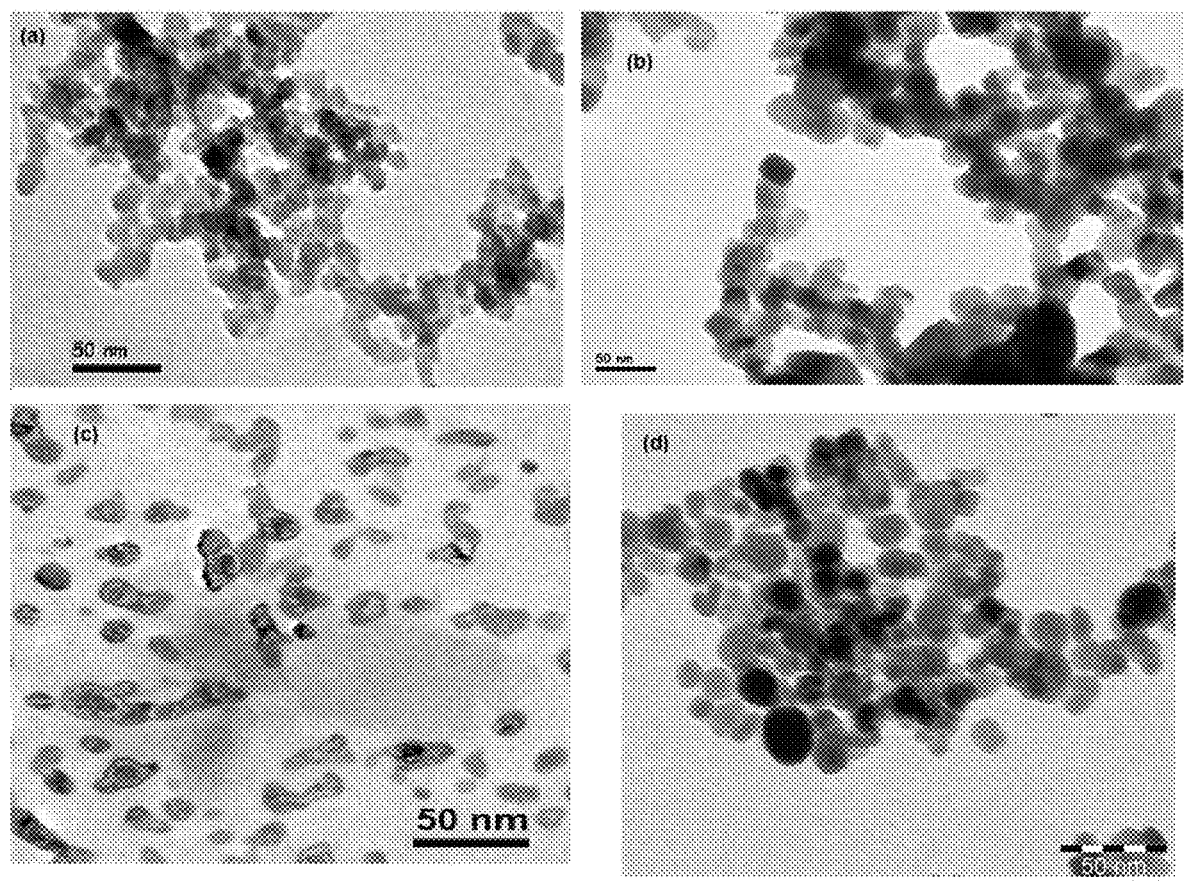
FIGS. 9A, 9B, 9C, and 9D show TEM micrographs of silica nanoparticles and their compositions with the present imidazolium ionic liquids.

The thermal stability and the contents of the $SiO_2$@CEO, $SiO_2$@CEOIm, $SiO_2$@CIm, $SiO_2$@DCIm, and $SiO_2$@DCTIm surfaces were determined from TGA thermograms represented in FIGS. 6A-6C. The TGA thermograms confirm the thermal stability of IILs were improved by incorporation of $Fe_3O_4$, $CaCO_3$ and $SiO_2$ NPs. The capping percentages (determined from RS % of thermograms FIGS. 4-6A-C) were increased on $SiO_2$>$Fe_3O_4$>$CaCO_3$ NPs.

The effect of DCTIm, DCIm, and CEOIm on the morphologies of $Fe_3O_4$, $CaCO_3$, and $SiO_2$ NP micrographs was investigated from TEM photos represented in FIGS. 7-9A-D. The uncapped $Fe_3O_4$, $CaCO_3$ and $SiO_2$ NPs show cubic, hexagonal, spherical aggregates having particle sizes ranging from 10 to 25 nm (FIGS. 7-9A). The use of DCTIm, DCIm, and CEOIm as capping agents for NPs lead to spherical morphologies with increasing particle diameters and dispersions (FIGS. 7-9B-D). The core/shell morphologies appeared on $CaCO_3$@DCIm and $CaCO_3$@DCTIm (FIGS. 8A and 8C). The particle sizes were increased up to 50-200 nm depending on the types, either inorganic or ILs types.

Figures 10A, 10B:
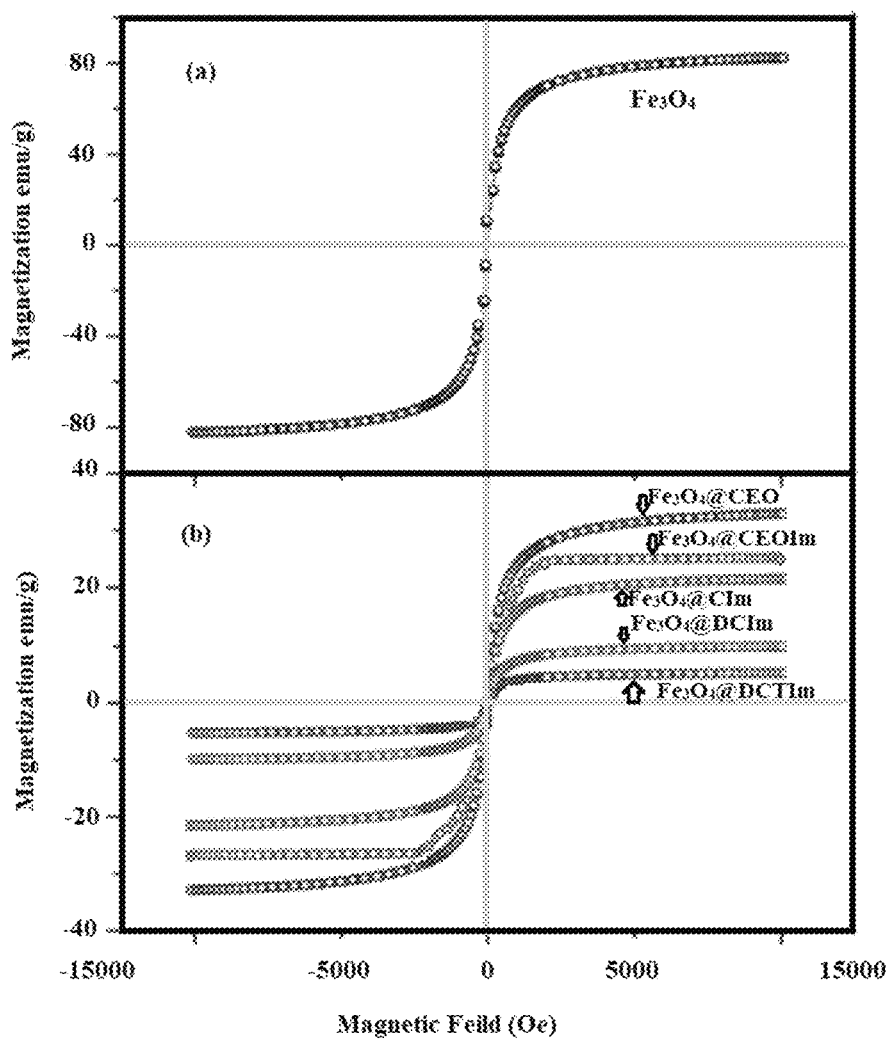
FIGS. 10A and 10B show magnetic hysteresis loops of magnetite nanoparticles capped with the present imidazolium ionic liquids.

The magnetic characterization of the $Fe_3O_4$, $Fe_3O_4$@CEO, $Fe_3O_4$@CEOIm, $Fe_3O_4$@CIm, $Fe_3O_4$@DCEIm, and $Fe_3O_4$@DCTIm were conducted using the superconducting quantum interference device at room temperature, with the maximum applied field up to 15 kOe (FIG. 10). The saturation magnetization (MS) and coercive force (HC) of the $Fe_3O_4$ was 78.1 emu/g and 250.9 Oe, respectively. However, MS and HC of the capped $Fe_3O_4$ with ILs were much smaller than uncapped. The decline in MS could be attributed to the presence of the nonmagnetic ILs. On the one hand, the presence of the hydroxyl groups $Fe_3O_4$@DCTIm (Example 3) provided magnetic nanoparticles with a limited nucleating location which effectively reduced the agglomeration of particles and reduced the saturation magnetization. In addition, HC was expected to decrease as the particle size increased (TEM images in FIGS. 7A-7C) indicated that HC of the composite was decreased due to the performance-related structural effects. The results confirm that the high magnetic properties can be ordered as $Fe_3O_4$@CEO>$Fe_3O_4$@CEOIm>$Fe_3O_4$@CIm>$Fe_3O_4$@DCEIm>$Fe_3O_4$@DCTIm.

Example 9

Application of Cardanyl Imidazolium ILs and their Nanoparticles as Oil Spill Dispersants Solutions of 50 g of any of the present synthesized compounds in 100 mL of ethanol were used to disperse oil spills. In brief, Saudi heavy crude oil (5 g) was added on the surface of 250 mL of sea water in a 500 mL beaker. The oil spill was stirred with a magnetic stirrer at 700 rpm to obtain a vortex with depth of 1 cm. Different magnetic to oil ratios (MOR) ranging from 1:1 to 1:100 were added to the crude oil mixture during 1 min. The stirring was stopped and 50 mL of the dispersed solution of crude oil in sea water was removed after 2 min. The dispersed crude oil in water (50 mL) was extracted with 50 mL of chloroform two times. The chloroform was evaporated using a rotary evaporator to determine the weight of extracted crude oil. The oil spill collection efficiency (OCE) was calculated as follows in Equation 1:

$$OCE = \frac{\text{Wt. of extracted crude oil} \times 500}{\text{Wt of crude oil}} \quad (1)$$

Example 10

Application of Magnetic Cardanyl Imidazolium Ionic Liquids as Oil Spill Collector The various capped magnetite nanoparticles prepared herein were used as oil spill collectors for heavy crude oil. In this regard, the magnetic materials based on $Fe_3O_4$@CEO, $Fe_3O_4$@CEOIm, $Fe_3O_4$@CIm, $Fe_3O_4$@DCEIm, and $Fe_3O_4$@DCTIm were used as oil spill collectors for heavy crude oil. Different magnetic cardanol to oil ratios (MOR) ranged from 1:1 to 1:100 were added to and their oil spill collection efficiency (OCE) was determined (per equation 1, above) and listed in Table 2, below.

TABLE 2

OCE data of the prepared magnetic imidazolium ILs

| Magnetic Cardanyl ILs | OCE (%) at different MOR | | | |
|---|---|---|---|---|
| | 1:1 | 1:5 | 1:25 | 1:100 |
| $Fe_3O_4$@CEO | 100 | 100 | 90 | 55 |
| $Fe_3O_4$@CEOIm | 100 | 100 | 95 | 65 |
| $Fe_3O_4$@CIm | 90 | 80 | 70 | 35 |
| $Fe_3O_4$@DCEIm | 100 | 100 | 85 | 45 |
| $Fe_3O_4$@DCTIm | 80 | 65 | 40 | 25 |

The order of magnetization of the prepared magnetic imidazolium ILs was determined as $Fe_3O_4$@CEO>$Fe_3O_4$@CEOIm>$Fe_3O_4$@CIm>$Fe_3O_4$@DCEIm>$Fe_3O_4$@DCTIm, as reflected in the data listed in Table 2. The most effective oil spill collector (Table 2) was based on those magnetic materials that achieved higher OCE data at higher MOR. It was noticed also that the suitable MOR (1:25) is effective to collect the heavy crude oil in the presence of magnetic Cardanyl imidazolium ILs ordered as $Fe_3O_4$@CEOIm>$Fe_3O_4$@CEO>$Fe_3O_4$@DCEIm. These results were attributed to their magnetic properties and their good dispersion in the heavy crude oil.

The data of $Fe_3O_4$@CEOIm, $Fe_3O_4$@CEO and $Fe_3O_4$@DCEIm magnetic imidazolium ILs after collection from the oil spill for different cycles occurred only for MOR (1:5) as represented in Table 3, below. The data listed in Table 3 elucidate that the $Fe_3O_4$@CEOIm and $Fe_3O_4$@DCEIm were effectively reused to collect heavy crude oil without losing their magnetization.

TABLE 3

OCE data to reuse magnetic imidazolium ILs at MOR (1:5)

| Magnetic Cardanyl ILs | OCE (%) at different MOR | | | |
|---|---|---|---|---|
| | Cycle 1 | Cycle 2 | Cycle 3 | Cycle 4 |
| $Fe_3O_4$@CEO | 100 | 95 | 90 | 80 |
| $Fe_3O_4$@CEOIm | 100 | 98 | 92 | 85 |
| $Fe_3O_4$@DCEIm | 100 | 100 | 95 | 90 |

Example 11

Application of Cardanyl Imidazolium Ionic Liquids and their Nanomaterials to Improve the Viscosity of Crude Oil All prepared materials as well as their nanomaterials based on magnetite, silica and $CaCO_3$ were used to improve the viscosity of the heavy crude oil to investigate their ability to disperse asphaltenes. Moreover, their ability to reduce interfacial tension, and wettability of sandstone and calcite rock, are another goal of the present work to apply in the field of heavy crude oil enhanced recovery.

The rheological behavior of a crude oil is highly influenced by its chemical composition, temperature, and the current, as well as previous thermal history. Crude oils exhibit a non-Newtonian character, often with a yield shear stress at and below their pour point temperature. Pretreatment of the crude oil is necessary for transportation of these crudes through the pipeline. Pretreatment of the crude oil with flow improver is one method by which the rheological character of the gelled crude is changed for easier transportation. The crude oil constituents in the crude oil i.e., asphaltenes, resins, lighter distillates, polar aromatics, etc., should be considered as important factors while ascertaining the flow behavior of a crude oil. Asphaltenes are very large heterogeneous molecules with condensed aromatic nuclei, which may associate to form colloidal sized particles that strongly influence the viscosity of the oil medium. To assure a realistic low temperature flow behavior of the tested crude oils, rheological measurements have to be evaluated. Hence, the additives based on Cardanyl ILs were evaluated for their performance as flow improvers in the tested crude oils through rheological measurements at concentration of 100, 250, 500, 1000, 2000, 5000 and 10,000 ppm. Measurements of the shear stress-shear rate relationship were carried out at a low temperature of 15° C.

The experimental procedure started with doping the crude with the additive at the prescribed concentration at 65° C.; meanwhile, the viscometer cup was preheated to the same temperature, then loaded with 25 ml of the heated sample, and the temperature was brought down at the test temperature (15° C.) at a low shear rate of 7.29 $S^{-1}$ (dynamic cooling). Shearing was continued for 15 min at the test temperature before evaluation. The shear stress-shear rate relationship was recorded for the tested samples. Experimental data were fitted to the Bingham plastic flow model using a linear regression computer program. The Bingham plastic flow model is represented by the equation 2:

$$\tau_{\eta p} = \tau_y + \frac{du}{dr} \quad (2)$$

where t is the shear stress (Pascal; Pa); ty is the yield shear stress (Pa); np, the plastic viscosity (milli-Pascal second; mPa·S); and du/dr is shear rate ($S^{-1}$).

The data of shear stress-shear rate relationships of crude without treatments, listed in Table 4 below, shows the plastic viscosity (mPa·S) and yield shear stress values (Pa).

TABLE 4

Rheological Data of heavy Crude Oil with Cardanyl imidazolium ILs at 15° C.

Rheological Data of BS Crude Oil

| Sample | Additive Concentration (PPM) | Yield Stress Value (Pa) | Plastic viscosity (mPa · S) | Correlation Coefficient |
|---|---|---|---|---|
| DCTIm | 0 | 142.6 | 234.7 | 0.9991 |
|  | 100 | 28.7346 | 95.706 | 1.0 |
|  | 250 | 26.7063 | 81.286 | 1.0 |
|  | 500 | 27.1088 | 76.478 | 1.0 |
|  | 1000 | 27.7015 | 69.93 | 1.0 |
|  | 2000 | 17.2883 | 50.185 | 1.0 |
|  | 5000 | 4.1662 | 44.978 | 1.0 |
|  | 10000 | 0.045 | 29.17 | 1.0 |
| CEIm | 100 | 58.7346 | 115.706 | 1.0 |
|  | 250 | 46.7063 | 61.286 | 1.0 |
|  | 500 | 37.1088 | 56.478 | 1.0 |
|  | 1000 | 37.7015 | 47.93 | 1.0 |
|  | 2000 | 27.2883 | 70.185 | 1.0 |
|  | 5000 | 10.1662 | 94.978 | 1.0 |
|  | 10000 | 8.7344 | 109.77 | 1.0 |
| CEOIm | 100 | 48.5346 | 125.306 | 1.0 |
|  | 250 | 43.2063 | 111.286 | 1.0 |
|  | 500 | 37.8088 | 106.478 | 1.0 |
|  | 1000 | 30.6015 | 99.93 | 1.0 |
|  | 2000 | 21.4883 | 80.185 | 1.0 |
|  | 5000 | 2.3662 | 40.978 | 1.0 |
|  | 10000 | 0.0324 | 25.17 | 1.0 |
| DCEIm | 100 | 38.7346 | 115.706 | 1.0 |
|  | 250 | 36.7063 | 91.286 | 1.0 |
|  | 500 | 34.1088 | 86.478 | 1.0 |
|  | 1000 | 33.7015 | 77.93 | 1.0 |
|  | 2000 | 27.2883 | 70.185 | 1.0 |
|  | 5000 | 16.1662 | 54.978 | 1.0 |
|  | 10000 | 4.7344 | 49.77 | 1.0 |

The data listed in Table 4 indicates that the tested crude oil possesses high yield shear stress values at low temperature. On the other hand, it was observed that the viscosity of crude oils was increased with cooling. The obtained data of np, ty and correlation coefficient were determined for tested crude oil as listed in Table 4. How a fluid obeys a given shear stress-shear rate relationship determines its class within the rheological classification of a fluid. A fluid is said to be Newtonian when it obeys Newtonian's law of viscosity, given by the equation (3):

$$\tau = \eta_p \frac{du}{dr} \quad (3)$$

So, a Newtonian fluid is one whose viscosity at a given temperature is independent of the shear rate. The viscosity of a Newtonian fluid at a given temperature is constant regardless of the viscosity, previous agitation or shearing of the fluid. For a Newtonian fluid, a linear plot of log t versus log du/dr gives a straight line. Moreover, the viscosity of a Newtonian fluid is not a function of the duration neither of shear nor of time laps between consecutive applications of shear rate.

The effect of structure and concentration of these polymers on rheological characteristics, such as viscosity and yield shear stress values, of crude oil were evaluated. The data of plastic viscosity and yield shear stress values were determined for all treated crude oil with Cardanyl imidazolium ILs tabulated in Table 4.

Figure 11:
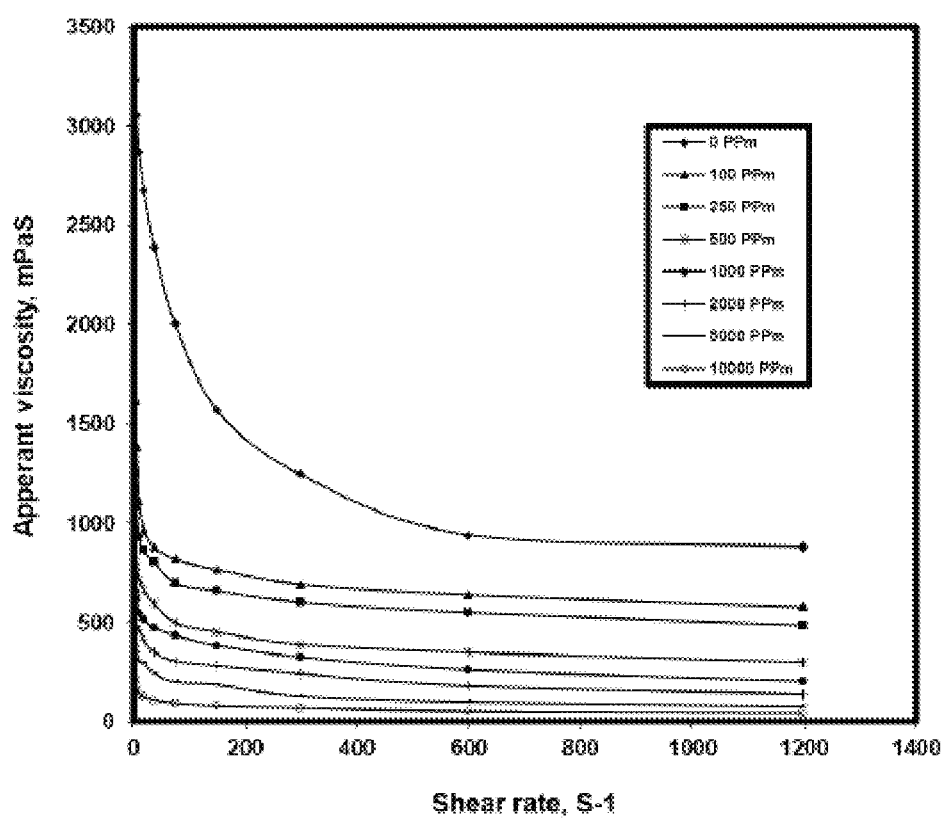
FIG. 11 is a graph showing the effect of DCEIm on the apparent viscosity of heavy crude oil at 15° C.

On the other hand, the apparent viscosities (mPa·S) of the untreated and treated crude oils with DCEIm were determined at constant temperature (15° C.) to evaluate their effects on the viscosities of crude and the results are shown as representative samples in FIG. 11. In this respect, the values of the plastic viscosity (mPa·S) and yield shear stress values (Pa) decreased by the addition of cardanyl imidazolium ILs even at high concentrations (10,000 ppm). The results listed in Table 4 indicate that the reduction in values of both viscosity and yield shear stress were strongly dependent on the type of the cardanyl imidazolium ILs. CEIm has a reduced efficiency at higher concentrations whereas CEOIm, which presents a poor performance at low concentrations, becomes better in more concentrated solutions. DCTIm achieves the best performance as lower viscosity values at a lower concentration. DCTIm and DCEIm exhibited a similar behavior, that is, they presented an optimum performance concentration at a concentration higher than CEOIm, but they maintained their capacity to reduce the crude pour point at higher concentrations. By comparing DCTIm and DCEIm, the minimum concentration to achieve the best performance is slightly higher for DCEIm than that for DCTIm.

Example 12

Application of Nanomaterials Capped with Cardanyl Imidazolium Ionic Liquids to Enhance the Recovery of Heavy Crude Oil Two types of nanomaterials, based on $SiO_2$ and $CaCO_3$, were selected to study enhanced oil recovery treatments for sand stone core (Table 1) and calcite core. The wetting characteristics of the seawater on the saturated rocks surface with crude oil (blank) and saturated samples against the dispersed nanoparticles capped with cardanyl imidazolium ILs seawater solution (10 wt. %) were evaluated from the contact angle measurements. The data of contact angles measurements on the sandstone rocks and calcite were represented in FIGS. 12 and 13, respectively.

Figure 12:
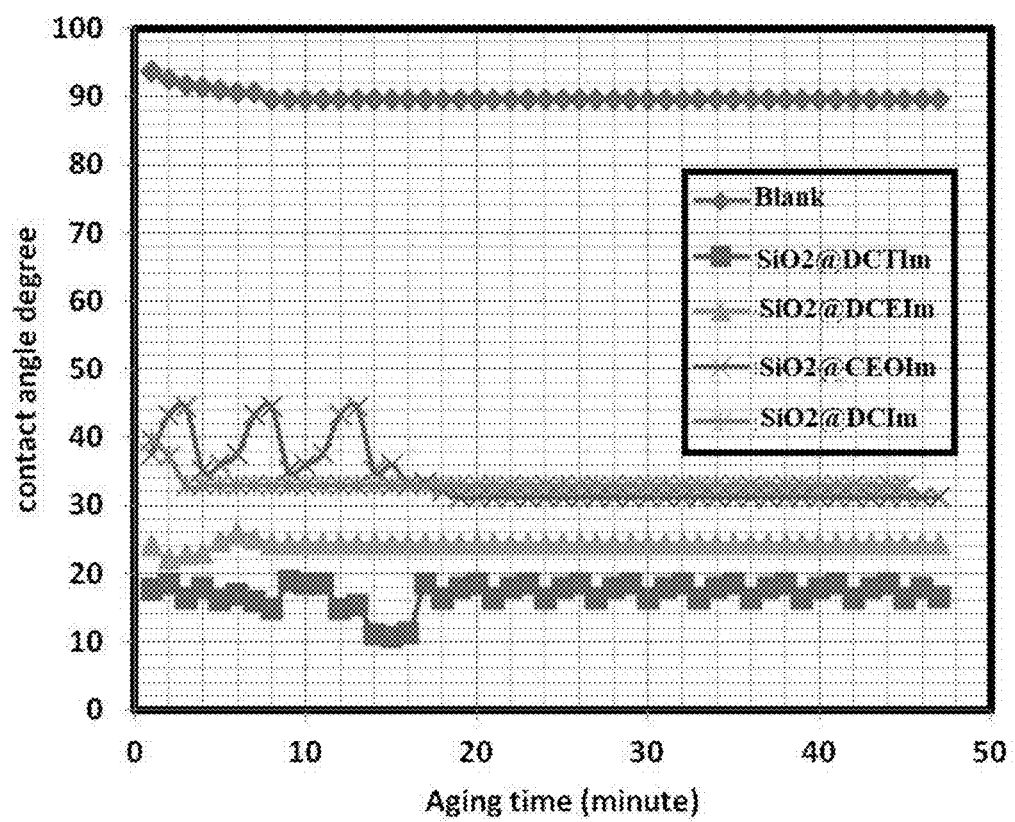
FIG. 12 is a graph showing contact angle data of seawater droplets and their dispersion of silica capped with the present imidazolium ionic liquids on dolomite rocks saturated with heavy crude oil.
Figure 13:
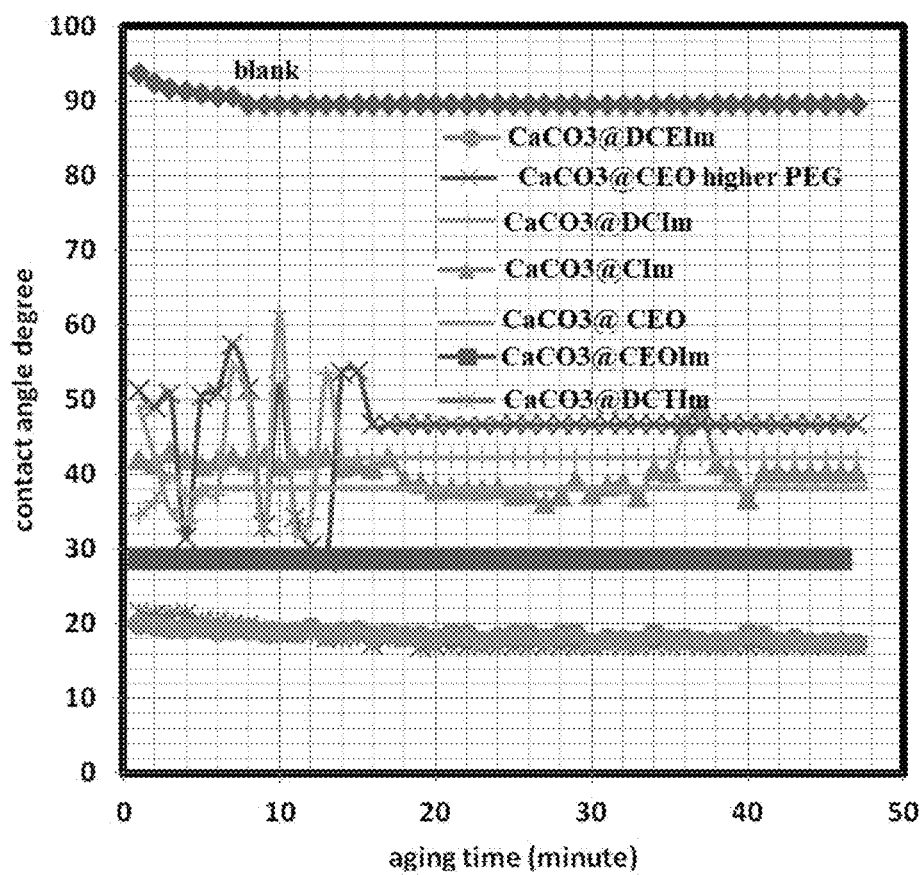
FIG. 13 is a graph showing contact angle data of seawater droplets and their dispersion of calcium carbonate capped with the present imidazolium ionic liquids on limestone rocks saturated with heavy crude oil.

It was noticed from FIGS. 12 and 13 that if water is injected into a water-wet core sample, then water invades the rock and displaces the oil with a flat fluid front and is expected to arrive everywhere along the exit surface. Depending on the surface wettability, the arriving fluid (water) might then either emerge as a thin film and quickly spread over the grains of the wetting (water wet) surface figure or emerge as individual droplets from the pores, repelled by the nonwetting (oil-wet) surface. The lower contact angles mean that the nanoparticles seawater solution have a great ability to displace the crude oil from the rocks and enhance their recovery.

The data indicated that $CaCO_3$@DCEIm (FIG. 13) and $SiO_2$@DCTIm (FIG. 12) were selected to be more effective nanomaterials to enhance the crude oil recovery from limestone and sandstone reservoirs. The IFT measurements of the crude oil and seawater solution of the dispersed $CaCO_3$ and $SiO_2$ NPs capped with cardanyl imidazolium ILs (10 wt. %) were measured and summarized in Table 5.

TABLE 5

Contact angles and IFT data of seawater droplets and their dispersion of silica capped with ILs with heavy crude oil

| Samples | Crude Oil | Interfacial tension mN/m concentration 10% in seawater at 25° C. | Contact angle concentration 1-% in seawater at 25° C. |
|---|---|---|---|
| CaCO$_3$@DCEIm | Arabian light crude | 27.3 | 29.3-33 |
| | Arabian heavy crude | 8.8 | 16-18 |
| SiO$_2$@DCTIm | Arabian light crude | 16.4 | 24-26 |
| | Arabian heavy crude | 6.5 | 11-14 |
| CaCO$_3$@CEO | Arabian light crude | 31.3 | 33-35 |
| | Arabian heavy crude | 8.5 | 46-48 |
| SiO$_2$@CEOIm | Arabian light crude | 30.4 | 50-53 |
| | Arabian heavy crude | 11.8 | 40-42 |
| CaCO$_3$@CEOIm | Arabian light crude | 21.4 | 32-33 |
| | Arabian heavy crude | 8.3 | 28-29 |
| SiO$_2$@DCIm | Arabian light crude | 25.6 | 24-26 |
| | Arabian heavy crude | 14.3 | 35-37 |
| CaCO$_3$@CIm | Arabian light crude | 33.4 | 40-42 |
| | Arabian heavy crude | 16.5 | 28-32 |
| CaCO$_3$@DCTIm | Arabian light crude | 30.1 | 46-50 |
| | Arabian heavy crude | 12.4 | 16-18 |
| SiO$_2$@DCEIm | Arabian light crude | 19.2 | 21-22 |
| | Arabian heavy crude | 6.5 | 17-18 |
| blank | Arabian light crude | 34.5 | 99-103 |
| | Arabian heavy crude | 36.5 | 96-98 |

The data show that the nanomaterials having the strong ability to lower the contact angles either in limestone or sandstone rocks have the same efficiency to reduce the IFT of either heavy or light crude oils.

Finally, these data prove that: firstly, the hydrophobic pore walls will become hydrophilic due to nanoparticle adsorption, and, consequently, the relative permeability of the oil phase increases, decreasing the resistance to oil flow, while at the same time, the relative permeability of the water phase decreases significantly. Second, oil in the small pores will be displaced due to nanoparticle adsorption and wettability changes, and the effective pore diameters for oil flow in the porous medium may, in turn, be enlarged. Finally, the adsorption of nanoparticles on the porous surface and blocking of the small pore throats may lead to reduction in porosity and absolute permeability of the porous media. The first and second effects are favorable for improving oil recovery, but the last effect has an unfavorable effect on oil production due to decrease in absolute permeability.

It is to be understood that the modified chemical structures of cardanol extracted from cashew nut shell oil, and the use of the same to prepare imidazolium ionic liquids are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for preparing a cardanol imidazolium ionic liquid, the method comprising:
    obtaining cardanol extracted from cashew nut oil;
    etherifying the cardanol with polyethylene glycol (PEG) to obtain a cardanoxy polyether surfactant (CEO);
    grafting the cardanoxy polyether surfactant (CEO) to an imidazole to obtain a grafted CEO imidazole; and
    quaternizing the grafted CEO imidazole to obtain a cardenyl polyethoxy imidazolium ionic liquid (CEOIm).

2. The method as recited in claim 1, wherein, in the etherifying step, the cardanol is mixed with the PEG, β,β-dicholorodiethylether (DCDE), toluene, and NaOH pellets, with the cardanol being mixed with the polyethylene glycol in an about 1:1 molar ratio.

3. The method as recited in claim 2, wherein the etherifying step further comprises removing NaCl precipitate, unreacted NaOH, unreacted toluene, unreacted DCDE, and unreacted PEG to obtain the cardenoxy polyether surfactant (CEO) in a yield of about 85% to about 90%.

4. The method as recited in claim 1, wherein the polyethylene glycol has a molecular weight of about 450 to about 2000 g/mol.

5. The method as recited in claim 1, wherein, in the grafting step, the cardenoxy polyether surfactant (CEO) is mixed with the imidazole, trimethylamine (TEA), 4-dimethylaminopyridene (DMAP), dry dichloromethane (DCM) and methanesulfonyl chloride (MSC) to obtain the grafted CEO imidazole.

6. The method as recited in claim 5, wherein the grafting step further comprises:
    dissolving the CEO, TEA, and DMAP in the DCM;
    adding the MSC to obtain a reaction mixture;
    adding further DCM to the reaction mixture to obtain a diluted reaction mixture;
    heating the diluted reaction mixture; and
    purifying the diluted reaction mixture to obtain the grafted CEO imidazole.

7. The method as recited in claim 1, wherein the quaternizing step is conducted by mixing the grafted CEO imidazole with an alkyl halide in a solvent followed by removing residual solvent, thereby providing an about 90% to about 95% yield of the cardenyl polyethoxy imidazolium ionic liquid (CEOIm).

* * * * *